US011582548B2

(12) United States Patent
Bui et al.

(10) Patent No.: US 11,582,548 B2
(45) Date of Patent: Feb. 14, 2023

(54) CUSHION FOR A HEARING PROTECTOR OR AUDIO HEADSET

(71) Applicant: 3M INNOVATIVE PROPERTIES COMPANY, St. Paul, MN (US)

(72) Inventors: Van Cuong Bui, Joenkoeping (SE); Caroline M. Ylitalo, Stillwater, MN (US); Caitlin E. Meree, St. Paul, MN (US); Patrick Hjort, Värnamo (SE); William Bedingham, Woodbury, MN (US); Assumpta A. G. Bennaars-Eiden, Andover, MN (US); Daniel B. Taylor, White Bear Lake, MN (US); Jonas A. Nilsson, Värnamo (SE); Richard C. Webb, St. Paul, MN (US); Andrew W. Long, Woodbury, MN (US); Henning T. Urban, Värnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 243 days.

(21) Appl. No.: 15/733,080

(22) PCT Filed: Nov. 21, 2018

(86) PCT No.: PCT/US2018/062252
§ 371 (c)(1),
(2) Date: May 13, 2020

(87) PCT Pub. No.: WO2019/104172
PCT Pub. Date: May 31, 2019

(65) Prior Publication Data
US 2020/0396532 A1    Dec. 17, 2020

(30) Foreign Application Priority Data
Nov. 21, 2017  (EP) ..................................... 17202717

(51) Int. Cl.
*H04R 1/00* (2006.01)
*H04R 1/10* (2006.01)
(Continued)

(52) U.S. Cl.
CPC ......... *H04R 1/1083* (2013.01); *A61B 5/0006* (2013.01); *A61F 11/14* (2013.01); *H04R 1/1008* (2013.01)

(58) Field of Classification Search
CPC ...... A61F 11/14; H04R 1/1083; H04R 1/1008
(Continued)

(56) References Cited

U.S. PATENT DOCUMENTS 3,721,993 A    3/1973 Lonnstedt
4,441,576 A    4/1984 Allen
(Continued)

FOREIGN PATENT DOCUMENTS

CA    1168589    6/1984
CN    90210086   7/1991
(Continued)

OTHER PUBLICATIONS

English Translation of Wu et al. Chinese Patent Publication 105213097, Jan. 6, 2016.*
(Continued)

*Primary Examiner* — Katherine A Faley
(74) *Attorney, Agent, or Firm* — Katherine M. Scholz

(57) ABSTRACT

A ring-shaped cushion for a hearing protector or audio headset. The cushion has a circumferential contact pad for sealing on a wearer's head and an attachment for sealing with an earmuff. The cushion further has a sound insulation tube that inwardly defines an inner space. The sound insulation tube extends between the contact pad and the attachment. The cushion has a ventilation passage that extends entirely through the cushion between an inlet opening in the
(Continued)

contact pad and an area outside of the inner space. The cushion may further include one or more physiological sensors to monitor the health of a wearer.

18 Claims, 9 Drawing Sheets

(51) Int. Cl.
  *A61B 5/00* (2006.01)
  *A61F 11/14* (2006.01)
(58) Field of Classification Search
  USPC .................................. 381/371, 372, 373
  See application file for complete search history.

(56) References Cited

U.S. PATENT DOCUMENTS

| | | | |
|---|---|---|---|
| 4,674,134 A | 6/1987 | Lundin | |
| 5,420,381 A * | 5/1995 | Gardner, Jr. | ............ C08G 18/48 |
| | | | 181/129 |
| 5,704,069 A | 1/1998 | Anderson | |
| 5,815,842 A | 10/1998 | Hiselius | |
| 5,970,160 A | 10/1999 | Nilsson | |
| 6,123,168 A | 9/2000 | Berg | |
| 7,024,013 B1 | 4/2006 | Van Dam | |
| 7,335,222 B1 | 2/2008 | Tyler | |
| 7,854,294 B2 | 10/2010 | Du | |
| 8,444,797 B2 | 5/2013 | Huang | |
| 8,550,206 B2 | 10/2013 | Keady | |
| 8,582,796 B2 | 11/2013 | Kimura | |
| 8,931,489 B2 | 1/2015 | Smith | |
| 9,071,894 B2 | 6/2015 | Galea | |
| 9,154,867 B2 | 10/2015 | Jenkins | |
| 2002/0083510 A1 | 7/2002 | Bavetta | |
| 2004/0045558 A1 | 3/2004 | Taylor | |
| 2007/0044205 A1 | 3/2007 | Sato | |
| 2007/0143907 A1 | 6/2007 | Hansson | |
| 2007/0226877 A1 | 10/2007 | Hansson | |
| 2008/0128198 A1 | 6/2008 | Du | |
| 2010/0307861 A1 | 12/2010 | Tiemens | |
| 2011/0002475 A1 | 1/2011 | Kimura | |
| 2012/0243699 A1 | 9/2012 | Michael | |
| 2013/0133671 A1 | 5/2013 | Fairclough | |
| 2014/0369537 A1 | 12/2014 | Pontoppidan | |
| 2016/0058375 A1* | 3/2016 | Rothkopf | ............. A61B 5/0261 |
| | | | 600/323 |
| 2017/0027758 A1 | 2/2017 | Hood, III | |
| 2017/0071495 A1 | 3/2017 | Denison | |
| 2017/0230744 A1 | 8/2017 | Schrader | |
| 2017/0339484 A1 | 11/2017 | Revyn | |
| 2018/0027158 A1* | 1/2018 | Tzvieli | ..................... H04N 5/33 |
| | | | 348/77 |
| 2018/0303392 A1 | 10/2018 | Everman | |
| 2018/0310893 A1 | 11/2018 | Everman | |

FOREIGN PATENT DOCUMENTS

| | | |
|---|---|---|
| CN | 2840574 | 11/2006 |
| CN | 201114705 | 9/2008 |
| CN | 103079136 | 5/2013 |
| CN | 203086674 | 7/2013 |
| CN | 203086675 | 7/2013 |
| CN | 203251414 | 10/2013 |
| CN | 203618107 | 5/2014 |
| CN | 105213094 | 1/2016 |
| CN | 105213096 | 1/2016 |
| CN | 105213097 | 1/2016 |
| CN | 105213098 | 1/2016 |
| CN | 105213101 | 1/2016 |
| CN | 105213102 | 1/2016 |
| CN | 105213103 | 1/2016 |
| CN | 105228042 | 1/2016 |
| CN | 105232226 | 1/2016 |
| CN | 205083776 | 3/2016 |
| CN | 205083778 | 3/2016 |
| CN | 205083781 | 3/2016 |
| CN | 205083786 | 3/2016 |
| CN | 205083787 | 3/2016 |
| CN | 205083789 | 3/2016 |
| CN | 205092945 | 3/2016 |
| CN | 105516842 | 4/2016 |
| CN | 205596284 | 9/2016 |
| DE | 2517703 | 11/1976 |
| DE | 2721935 | 11/1978 |
| DE | 9012732 | 12/1990 |
| EP | 0095902 | 12/1983 |
| EP | 1075164 | 2/2001 |
| EP | 2053874 | 4/2009 |
| GB | 2527157 | 12/2015 |
| WO | WO 1994-017763 | 8/1994 |
| WO | WO 1994-017764 | 8/1994 |
| WO | WO 1996-023462 | 8/1996 |
| WO | WO 2005-122983 | 12/2005 |
| WO | WO 2009-018677 | 2/2009 |
| WO | WO 2010-111013 | 9/2010 |
| WO | WO 2017-007379 | 1/2017 |
| WO | WO 2017-136386 | 8/2017 |
| WO | WO 2018-150351 | 8/2018 |

OTHER PUBLICATIONS

Frase, "Cleaning and Sanitising", 6 pages.
International Search report for PCT International Application No. PCT/US2018/062252 dated Jan. 28, 2018, 3 pages.
Extended EP Search Report, EP 18881311.7, dated Sep. 2, 2021 (9 pages).

* cited by examiner

CUSHION FOR A HEARING PROTECTOR OR AUDIO HEADSET

CROSS REFERENCE TO RELATED APPLICATIONS

This application is a national stage filing under 35 U.S.C. 371 of PCT/US2018/062252, filed Nov. 21, 2018, which claims the benefit of EP Application No. 17202717.9, filed Nov. 21, 2017, the disclosure of which is incorporated by reference in its/their entirety herein.

FIELD OF THE INVENTION

The invention relates to a nonporous, in particular foam-free cushion for a hearing protector or audio headset, and a hearing protector or audio headset comprising such a cushion. The cushion is particularly provided with a ventilation passage that establishes fluid communication between the skin of a wearer of the hearing protector or audio headset and the environment.

BACKGROUND ART

Hearing protectors are typically used in noisy environments for protecting a wearer's hearing from noise at potentially harmful noise levels. Typically, hearing protectors have two muffs or caps which cover the ears of the wearer and which are connected to one another by a headband. Each cup further typically is formed by a rigid shell that is furnished with a noise dampening material, for example a foamed material.

There is a general desire to make hearing protectors user-friendly, in particular to encourage persons that are in noisy environments for longer times to actually wear the protectors. Often a wearer sweats in an area in which the hearing protector is in contact with the wearer's skin. There are hearing protectors which are furnished with materials that have moisture absorbent properties.

For example U.S. Pat. No. 5,704,069 discloses the use of a superabsorbent nonwoven material in a moisture absorbing cover for an earmuff. A moisture absorbing ring-shaped cover for a sealing ring of an earmuff includes an inner layer of super-absorbent fiber material.

Although existing active hearing protectors have a variety of advantages there is still a need for a hearing protector which provides maximized wearing comfort and which is relatively inexpensive.

SUMMARY OF THE INVENTION

The invention relates to cushion for a hearing protector or audio headset. In particular the cushion is ring-shaped so as to encircle a wearer's ear when the hearing protector or audio headset is worn. The cushion comprises a contact pad for sealing on a wearer's head. The cushion further comprises an attachment for sealing with an earmuff. The cushion further has a sound insulation tube. An inner space may be defined inwardly of the tube.

The sound insulation tube extends between the contact pad and the attachment. The sound insulation tube preferably forms a ring-shaped airtight seal between the contact pad and the attachment. Further, the sound insulation tube preferably forms the only ring-shaped airtight seal that connects the contact pad and the attachment. The cushion comprises a ventilation passage that extends entirely through the cushion between an inlet opening in the contact pad and an area outside of the inner space. In particular the ventilation passage does not end in a closed or hermetically sealed chamber.

The cushion is thus provided with a ventilation passage that establishes fluid communication between the skin of a wearer of the hearing protector or audio headset and the environment.

The invention is advantageous in that it provides for a cushion that allows moisture and/or heat eventually present in an area between the wearer's skin and the cushion to escape to the environment outside the hearing protector or headset. Therefore the invention helps maximizing the wearing comfort of the hearing protector or headset. Further the invention provides for a cushion that does not require any porous or foamed material. Thus, the cushion is made of a material that does not soak up liquids, like for example sweat and/or cleaning agents. Accordingly the cushion of the invention is easy to clean and can be easily maintained in a clean condition. Therefore the cushion of the invention helps maximizing the hygiene in use of the hearing protector or headset. In addition the cushion of the invention is easy to mold in one piece and thus helps minimizing the manufacturing costs.

The sound insulation tube is preferably ring-shaped. Further, the sound insulation tube is preferably formed by a circumferential wall. The inner space may be defined between opposite surface portions of the circumferential wall, which face each other. Preferably the cushion extends along the ring-shape at an open profile, for example a C-shaped or generally C-shaped profile. (In contrast an O-shaped or ring-shaped profile is a closed profile). The profile may be formed by a section of the attachment, a section of the sound insulation tube and a section of the contact pad. The sound insulation tube is preferably connected at one end to the attachment and at an opposite end to the contact pad. The attachment and the contact pad are preferably only connected to each other via the sound insulation tube.

The term "environment" for the purpose of the present specification particularly refers to an area outside the hearing protector or headset and outside an area encapsulated around a wearer's ear by the hearing protector or headset when worn by a wearer. The environment is therefore in fluid communication with those portions of the wearer's head that are not encapsulated by the hearing protector. Further, when the hearing protector is worn by a wearer the ventilation passage is preferably in fluid communication with those portions of the wearer's head that are not encapsulated by the hearing protector.

Preferably the ventilation passage establishes a fluid connection between the inlet opening in the contact pad and the environment. In particular, the ventilation passage may establish a fluid connection between the inlet opening in the contact pad and the area outside of the inner space. The inner space corresponds to a space that is encircled or surrounded by the sound insulation tube. The cushion may be further defined within a three-dimensional Cartesian coordinate system having an X-, Y- and Z-axis. The contact pad preferably has a major head facing surface. The head facing surface is typically that surface of the cushion that is in direct contact with the wearer's head when the hearing protector or headset is worn. The contact pad preferably extends with the head facing surface parallel to a plane defined by the X-axis and the Y-axis, and the attachment is preferably offset relative to the contact pad along the Z-axis. The sound insolation tube may extend around an axis that is parallel to the Z-axis.

The audio headset may be a hearing protector that includes a loudspeaker. Further, the contact pad preferably extends circumferentially. Thus the contact pad is adapted for sealing with a wearer's head along a closed path around the wearer's ear. This helps maximizing the attenuation of the hearing protector.

The cushion is preferably nonporous, in particular foam-free. The term nonporous as referred to herein means a material that has at least 90% of its theoretic density. A suitable silicone material for making the cushion may for example have a theoretical density of between 1.1 g/cm$^3$ and 1.2 g/cm$^3$.

The sound insulation tube is preferably non-permeable with respect to air. Thus the sound insulation tube can act a sound barrier.

In an embodiment the cushion comprises a plurality of inlet openings. The ventilation passage of this embodiment extends between the plurality of inlet openings in the contact pad and an area outside of the inner space. In other words in this embodiment one end of the ventilation passage is formed by the plurality of inlet openings. Preferably the inlet opening or inlet openings are arranged within the contact pad so that at least a portion of the contact pad adjacent the sound insulation tube forms a circumferential ring or closed path. Therefore the contact pad has a circumferential and contiguous ring-shaped first surface area for sealing with a wearer's head. This helps ensuring that a wearer's ear is sealingly encapsulated by the hearing protector or headset. This further helps ensuring a good protection from noise. The contact pad preferably further has a total surface area which is greater than the first surface area. Thus any force exerted by the contact pad to a wearer's head is distributed over a relatively large surface although the first surface area that actually provides the sealing with the wearer's head is relatively small. This contributes to a maximized wearing comfort.

In one embodiment the inlet opening or the inlet openings provide an open area. The open area of the plurality of inlet openings can be determined from a sum of partial open areas of the individual inlet openings. Further the contact pad outside the inlet opening or openings provides the total surface area. This means that the total surface area does not include the open area. The ratio of the open area relative to the total surface area is preferably below 50%, more preferably within a range of 30% to 45%, for example about 35%. Preferably the contact pad is not permeable in the total surface area. In particular the contact pad is preferably not made of a fabric.

In one embodiment the contact pad protrudes radially or essentially radially outwardly from a proximal side of the sound insulation tube. The proximal side of the sound insulation tube is that side adjacent the contact pad, whereas a distal end of the sound insulation tube is preferably arranged adjacent the attachment. The sound insulation tube and the contact pad are preferably monolithically formed in one piece.

In an embodiment the cushion, adjacent an outer circumference of the contact pad, further comprises a circumferential collar. The collar preferably protrudes from the contact pad in a direction toward the attachment. The collar and the contact pad are preferably monolithically formed in one piece. Accordingly, the sound insulation tube, the contact pad and the collar are preferably monolithically formed in one piece.

In a further embodiment a gap is provided between a free end of the collar and the attachment. The material and the structure of the cushion provides the cushion with a resilient property. This is to allow that the cushion adapts tightly and sealingly with a wearer's skin. A compression of the cushion (in a dimension parallel to the Z-axis) preferably causes the gap to close such that the contact pad is supported on the attachment via the collar. This is because a force acting on the cushion in a dimension of the Z-axis causes the sound insulation ring to deform. Therefore the contact pad and the attachment move toward each other until the collar touches the attachment. In a situation in which the gap exists the compression is based on a first modulus of resilience. And in a situation in which the collar abuts the attachment the compression is based on a greater second modulus of resilience. This allows moving the hearing protector or headset on a wearer's head with the contact pad being in contact with the wearer's skin at a relatively low pressure force as provided via the first modulus of resilience. This helps maximizing the wearing comfort because the hearing protector or headset can be comfortably positioned to the desired location on the wearer's head.

The gap further allows for earpieces of glasses or goggles to be inserted within the gap of the cushion. This helps avoiding that the hearing protector is worn on the earpieces extending around a wearer's ear where they may cause a leakage between the cushion and the wearer's head.

In a further embodiment the collar in a direction away from the contact pad (in a dimension parallel to the Z-axis) tapers. This means that the collar in a direction away from the contact pad reduces in cross-sectional dimension. This helps maximizing the support of the contact pad because the tapering collar tends less to buckle under load than a non-tapering collar.

In one embodiment the collar comprises one or a plurality of outlet openings of the ventilation passage. Preferably the sound insulation tube, the contact pad and the collar in combination with the attachment define a ring-shaped chamber inside the cushion. The inlet opening or inlet openings as well as the outlet opening or outlet openings are preferably in fluid communication with the ring-shaped chamber. Thus the ventilation passage is formed by through-holes through the contact pad forming the inlet opening(s), further through-holes through the collar forming the outlet opening(s) and the ring-shaped chamber. Preferably, in a situation in which the hearing protector is not worn by a wearer, the inlet opening and the outlet opening are in fluid communication not only via the ventilation passage but also via a path outside the ventilation passage (or via the environment).

In one embodiment the cushion further comprises a circumferential resilient dividing wall protruding from the contact pad in a direction toward the attachment, providing a gap between a free end of the dividing wall and the attachment, and wherein a compression of the cushion causes the gap to close such that a closed volume is formed between the dividing wall and the sound insulation tube. The dividing wall is arranged in the chamber circumferentially around the inner space and subdivides the chamber into two coaxial ring-shaped compartments when the hearing protector is worn, with one compartment (the "inner compartment") being closer to the sound insulation tube and the other compartment (the "outer compartment") being closer to the collar. The dividing wall extends, in the chamber, from the contact pad toward the attachment, essentially parallel to the sound insulation tube. The foot of the dividing wall is on the contact pad between the sound insulation tube and the collar. The dividing wall extends toward the attachment far enough for its free end to contact the attachment when the hearing protector is worn, i.e. when there is pressure on the contact pad. The dividing wall extends toward the attachment only so far as its free end to leave a gap between the dividing wall and the attachment when the hearing protector is not worn, i.e. if there is no pressure on the contact pad.

When the hearing protector is worn, the free end of the dividing wall contacts the attachment and thereby separates the inner compartment from the outer compartment. In this situation the outer compartment remains in communication with the outside space through the outlet openings, while the inner compartment now forms a separate, closed volume of air around the inner space, not in communication with the outer compartment or with the outside space. Thereby the inner compartment provides additional sound insulation.

In one embodiment the attachment comprises a seal for sealing with an earmuff. The seal may be formed by a sealing rim that extends circumferentially and that protrudes from the attachment in a direction from the contact pad to the attachment.

In one embodiment the cushion further comprises a mounting ring. The cushion may further comprise a, preferably circumferential, attachment flange that protrudes radially outwardly from the distal side of the sound insulation tube. The mounting ring preferably comprises the seal, in particular the sealing rim. Further, the attachment flange is sealingly attached (in particular bonded, welded or molded) on the mounting ring. The sound insulation tube and the attachment flange are preferably monolithically formed in one piece. Accordingly, the sound insulation tube, the contact pad, the collar and the attachment flange are preferably monolithically formed in one piece.

In one embodiment at least the contact pad is made of a material exhibiting a Shore hardness A within a range of 20 to 40. Preferably the sound insulation tube, the contact pad, the collar and the attachment flange are made of a material exhibiting a Shore hardness A within a range of 20 to 40. Preferably contact pad and preferably also the sound insulation tube, the collar and the attachment flange are is made of silicone. The sound insulation tube, the contact pad, the collar and optionally the sealing rim are preferably made of the same material, for example from a silicone or rubber material.

In one embodiment the cushion further comprises a nonporous and cup-shaped sound attenuator for insertion into an earmuff. The sound attenuator is preferably arranged adjacent the attachment of the cushion. For example the sound attenuator may be molded in one piece with the cushion or may be hingedly connected to the cushion. Further, the sound attenuator preferably has an outer attenuator shell and a plurality of sound-attenuating structures which protrude from the attenuator shell. The attenuator shell is preferably cup-shaped, thus forming an interior room, and the sound-attenuating structures preferably protrude within the interior room. The sound-attenuating structures may be pins or cones that are arranged in at least one group. The sound-attenuating structures are preferable spaced from each other so that the closest distance between two neighboring sound-attenuating structures (side-to-side spacing) is smaller than the distance of the centers of two neighboring sound-attenuating structures (center-to-center spacing). Thereby narrow air gaps are provided by the sound-attenuating structures which provide for sound attenuation. Preferably the cushion is monolithically formed in one piece with the sound-attenuator. Accordingly the cushion and the sound-attenuator can be molded. Due to the absence of any porous, in particular foamed, material the cushion including the sound-attenuator is washable. This helps maximizing the hygiene level in use of the hearing protector or headset.

In certain embodiments, the cushion is homogenously molded. Trials have shown that a homogenously molded cushion provides for a more even, i.e. flatter, sound attenuation performance across the relevant sound frequencies. A flat sound attenuation performance facilitates perception of audible warning signals and provides for a more natural sound to the user.

In certain embodiments, the cushion houses one or more physiological sensors, such as photoplethysmograph sensors, electroencephalogram sensors, or other similar optical or electrophysiological sensing devices. In some examples, a physiological sensor may detect brain activity and/or electrodermal activity. Another example physiological sensor may detect biomarkers and/or blood oxygen saturation, indicating heart and respiration rates, blood pressure, and/or body temperature. In certain embodiments, the one or more physiological sensors may be in communication with a computing system, stored either locally within the cushion and/or hearing protector or remotely (e.g. a cloud-based computing network, mobile device, data-logging device, fusion hub, etc.), configured to analyze the signals output by the sensors, and output an alert, and/or an indication of an alert, if the computing device detects a high probability of an adverse physiological condition, such as fatigue and drowsiness, dehydration, excessive body temperature, seizures, or loss of consciousness.

In certain embodiments, the cushion comprises at least one physiological sensor disposed within the ventilation passage that extends entirely through the cushion, wherein the at least one physiological sensor is configured to generate signal data associated with one or more physiological parameters of the wearer.

In certain embodiments, a system includes a hearing protector comprising two earmuffs for positioning on a head of a wearer, an earmuff cushion having at least one physiological sensor as described in the examples above, and a computing device with processing circuitry configured to receive, from the at least one physiological sensor, the signal data associated with the one or more physiological parameters of the wearer, and output, based on the signal data, an alert associated with a physiological condition of the wearer.

In some embodiments both earmuffs of a hearing protector comprise a physiological sensing device, wherein the two sensing devices may be identical devices for redundancy or measured data or the two sensing devices may be different sensing devices, measuring different physiological signals of the wearer of the hearing protector.

In a further aspect the invention relates to hearing protector or headset that comprises an earmuff and a cushion of the invention. In particular the hearing protector or headset may have two earmuffs, and a cushion of the invention is mounted to each of the earmuffs. The hearing protector or headset may further comprise a headband for holding the earmuffs. Further the hearing protector or headset may be furnished with a loudspeaker and optionally with electronic circuitry for driving the loudspeaker.

When washing a hearing protector in high-temperature industrial washing machines the final sanitizing must normally be at least 82° C. for at least 30 seconds. All items should be air-dried after washing. Silicone material in the cushion and in the sound absorbing insert can generally withstand higher temperatures, to be able to be washed at 85° C. Hearing protectors must also be able to withstand washing at 82° C., probably even above 85° C. since some washers run at that temperature. Therefore, in one embodiment, the hearing protector described above comprises a headband, wherein the cushions, the headband and the earmuffs are each made from a respective heat-resistant material, such as a plastic material or a metal, that can withstand industrial washing at 85° C. The headband may be made from a heat resistant plastic, optionally in combination with steel.

DETAILED DESCRIPTION OF THE INVENTION

Figure 1:
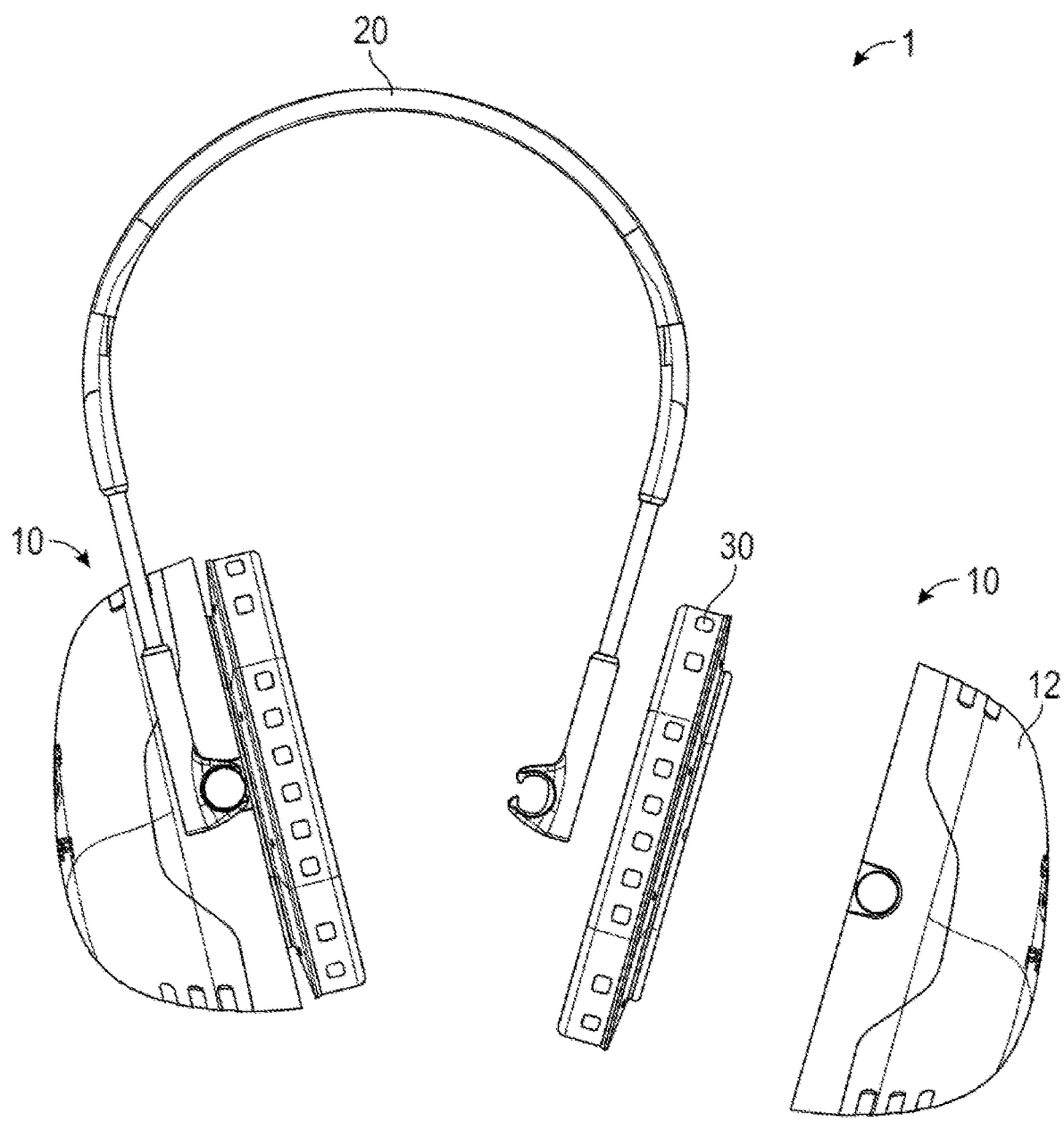
FIG. 1 is a partial exploded view of a hearing protector according to an embodiment of the invention.

FIG. 1 shows a hearing protector 1 according to the invention. The hearing protector 1 comprises two earmuffs 10. One of the earmuffs 10 is illustrated as exploded view for the sake of explanation only, although it is typically assembled. The earmuff 10 in the example is a passive earmuff, although in another example an active earmuff may be provided. Typically an active earmuff has electronic components such as a loudspeaker and/or a microphone, whereas a passive earmuff does not have such electronic components.

The earmuff 10 has an earmuff shell 12 and a cushion 30. The earmuff shell 12 is provided with noise dampening properties. For example, the earmuff shell 12 may be formed of a rigid material and may be provided with a sound attenuator (as visible in FIG. 3) inwardly. Such rigid material may be a plastic material, for example acrylonitrile butadiene styrene (ABS). As outlined in more detail below, the cushion 30 is made from or may comprise a soft structure and/or material that enables the cushion 30 to adapt to a wearer's head around the wearer's ear. Thus, the cushion 30 can seal at the wearer's head.

The hearing protector 1 further has a headband 20 to which the earmuffs 10 are attached. The earmuffs 10 in the example are hingedly attached at opposite sides of the headband 20. Thus, the earmuffs 10 can automatically freely orient relative to the wearer's head when the hearing protector 1 is worn by a wearer. Such free orientation provides for the cushion 30 to uniformly seal with the wearer's head along a circumference of the cushion 30.

Figure 2:
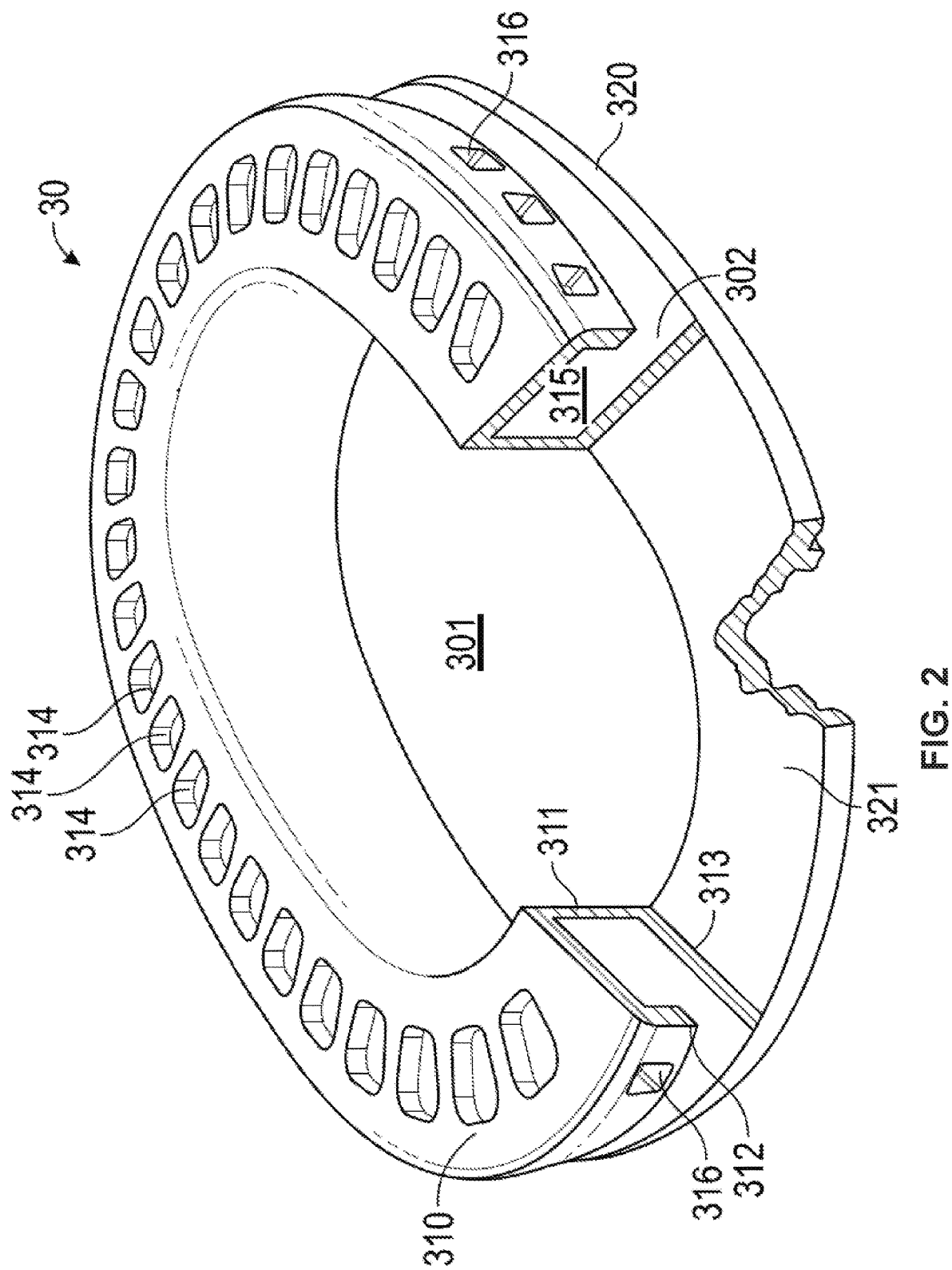
FIG. 2 is a perspective view of a cushion for a hearing protector according to an embodiment of the invention.

FIG. 2 shows the cushion 30 in more detail. It is noted that the Figure illustrates a cutout for explanation only, although the cushion 30 has a closed ring shape (as apparent from FIG. 3). The cushion 30 has a contact pad 310 for sealing on a wearer's head around the ear. The cushion 30 on the opposite side of the contact pad 310 comprises an attachment 320. The attachment 320 is configured for sealing with an earmuff, for example as shown in FIG. 1. The cushion 30 further has a sound insulation tube 311 that connects the contact pad 310 and the attachment 320. The sound insulation tube 311 is a circumferential wall that is non-permeable with respect to air. Therefore the wall hinders sound in permeating through the wall. It is noted that the term "non-permeable" does not exclude a permeation in the sense of a long-term permeation of gases between molecules of the wall. In particular the wall preferably does not have any macroscopic through-holes and is not a fabric. The sound insulation tube forms an inner space 301 which is sized to accommodate an ear of a wearer of the hearing protector.

The cushion 30 further comprises a collar 312 which protrudes from the contact pad 310 in a direction toward the attachment 320. The sound insulation tube 311, the contact pad 310, the collar 312 and an attachment flange 313 are monolithically formed in one piece. The attachment flange 313 in the example is attached on a mounting ring 321. Thus the attachment flange 313 provides for a fixed connection of the sound insulation tube 311 with the mounting ring 321. Further, due to the monolithic structure of the combination of the sound insulation tube 311 and the contact pad 310 a fixed connection of the sound insulation tube 311 and the contact pad 310 is provided. The skilled person will recognize that in the connection between the sound insulation tube and the mounting ring and/or the sound insulation tube and the contact pad may be provided otherwise, for example by welding or adhesive bond. The sound insulation tube 311, the contact pad 310, and the collar 312 are preferably made of a resilient material, for example silicone or a thermoplastic elastomer, like thermoplastic urethane. Thus, the cushion is provided with resilient and adaptable properties. This ensures a good sealing of the cushion with a wearer's head and helps maximizing wearing comfort.

A gap 302 is provided between the collar 312 and the attachment 320. A compression of the cushion 30 causes the gap to reduce until the collar 312 abuts on the attachment 320. In a situation in which there is a gap between the collar 312 and the attachment 320 the contact pad 310 is only supported by the sound insulation tube 311. Accordingly the properties of the sound insulation tube 311 provide for a first modulus of resilience of the cushion 30 in a situation in which the gap exists. Further, once the collar 312 abuts on the attachment 320 the contact pad 310 is supported by the sound insulation tube 311 as well as by the collar 312. Accordingly once the collar abuts on the attachment 320 the combination of the properties of the sound insulation tube 311 and the properties of the collar 312 provide for a second modulus of resilience of the cushion 30. The second modulus of resilience is greater than the first modulus of resilience. Due to the support of the contact pad 310 by the collar 312 the contact pad 310 is supported on the inner circumference as well as on the outer circumference. Thus once the collar 312 abuts on the attachment any further compression of the cushion 30 causes the contact pad 310 to resiliently move parallel (or essentially parallel) to major surfaces of the contact pad 310. One of the major surfaces is formed by the surface of the contact pad 310 which is in direct contact with the wearer's head when the hearing protector is worn.

The contact pad 310 comprises a plurality of inlet openings 314 (not all being provided with reference lines in the Figure). Each inlet opening 314 is formed by a through-hole through the contact pad 310 and is in fluid communication with a chamber 315 formed between the contact pad 310 and the attachment 320. Further a plurality of outlet openings 316 (not all being provided with reference lines in the Figure) are provided in the collar 312. The outlet openings open the chamber 315. Therefore in a situation in which the cushion 30 is worn by a wearer fluid communication is provided between the outlet openings 316 and the wearer's skin via the chamber 315 and the inlet openings 314. In other words, the cushion 30 comprises a ventilation passage that extends entirely through the cushion 30 between the inlet openings 314 and the outlet openings 316. Thus moisture, for example from sweating of a wearer, can escape through the cushion 30 to an exterior of the cushion, while the cushion air-tightly seals a space around the wearer's ear. Further, because the cushion 30 is foam-free and free of any open porous material the cushion 30 does not soak any moisture from the wearer's skin. This helps maximizing comfort and hygiene, for example in case a hearing protector is shared by different wearer's.

The cushion 30, in the example particularly the mounting ring 321, further has a circumferential sealing rim 322. The sealing rim 322 is configured to sealingly snap into the earmuff shell of the earmuff (for example as shown in FIG. 1). The sealing rim 322 may be made of or may be coated with the same material as the sound insulation tube, the contact pad 310 and the collar 312 or may be made of or coated with a different, preferably resilient, material.

Figure 3:
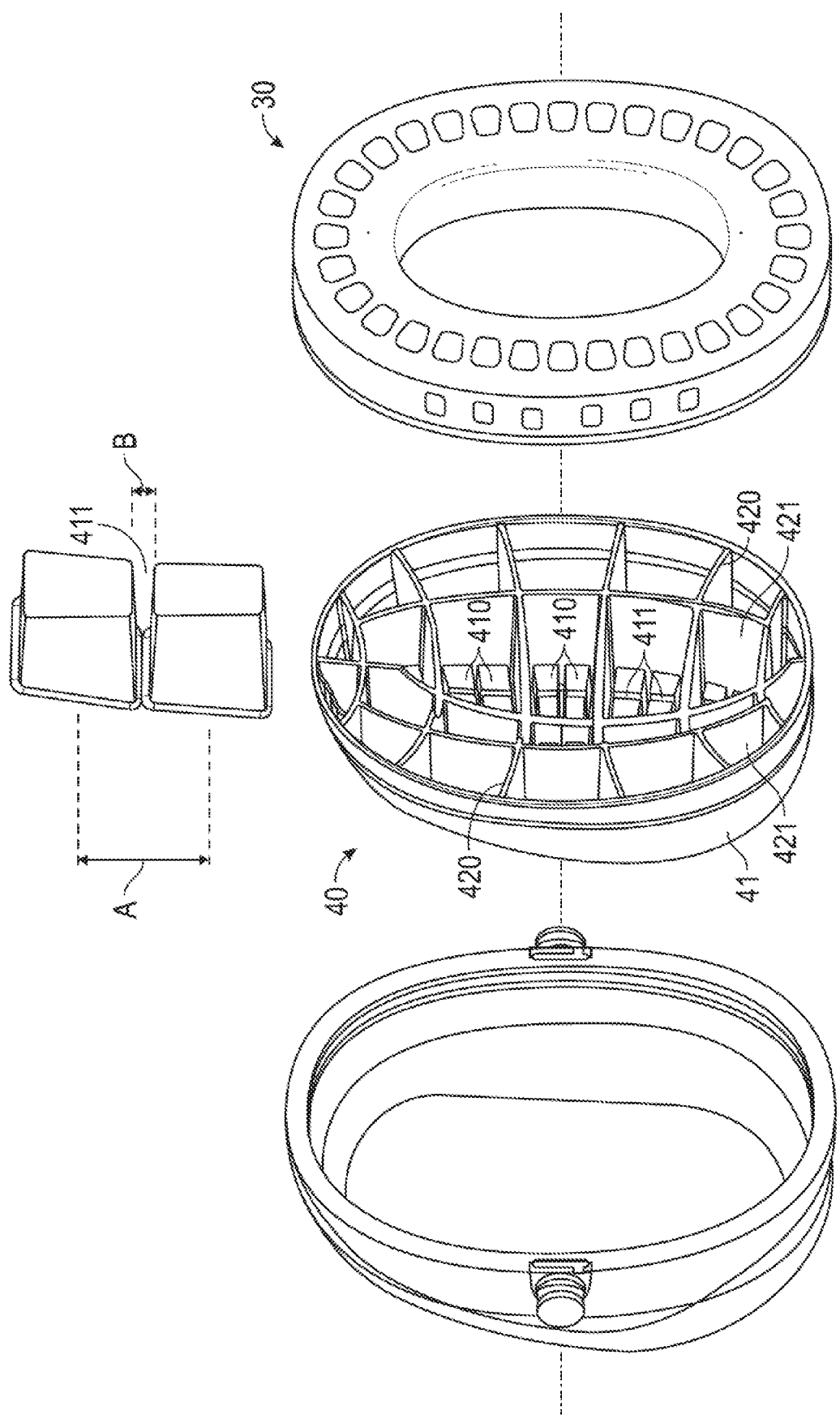
FIG. 3 is an exploded perspective view of a cushion in combination with a sound attenuator for a hearing protector according to an embodiment of the invention.

FIG. 3 shows the cushion 30 in combination with a sound attenuator 40. Such a sound attenuator is for example disclosed in detail in U.S. Application No. 62/459,768 filed on Feb. 16, 2017. Although illustrated as two pieces, the cushion 30 and the sound attenuator 40 are preferably formed in one piece. The cushion 30 and the sound attenuator 40 may be monolithically formed, for example molded, or they may be molded by two-shot injection molding with one component (the cushion 30 or the sound attenuator 40) molded onto the other (sound attenuator 40 or the cushion 30, respectively). The sound attenuator 40 may be made of the same material as the combination of the sound insulation tube, the contact pad and the collar of the cushion shown in FIG. 2, or of an alternative, preferably resilient, material.

The sound attenuator 40 is nonporous and in particular foam-free. Therefore the sound attenuator 40 is washable and thus can help maximizing the hygiene in the use of the hearing protector. In more particular, the sound attenuator 40 has a cup-shaped attenuator shell 41 from which a plurality of sound-attenuating structures 410. The sound-attenuating structures 410 in the example protrude at a square or rectangular cross-section. Further, the sound-attenuating structures 410 have a length in a dimension along which sound-attenuating structures 410 protrude and a first and a second width perpendicular to the length and perpendicular to each other. In the example the first and second width are the same and each or the first and the second width are less that the length. Each of the sound-attenuating structures 410 form major side surfaces facing in directions laterally, in particular transverse, from the dimension of the length. In the example the sound-attenuating structures 410 are cuboid-shaped and therefore have four major side surfaces. It is however noted that in another example the sound-attenuating structures 410 may protrude at a triangular, hexagonal or other shape, but preferably form a space between each two sound-attenuating structures that is uniform at least in a plane perpendicular to the dimension of the length. For example, a plurality of concentric rings is encompassed.

In the example the sound-attenuating structures 410 are spaced at a center-to-center spacing A and a side-to-side spacing B. The side-to-side spacing B is measured between opposite side surfaces of two neighboring sound-attenuating structures 410. Preferably the side-to-side spacing B is smaller than the center-to-center spacing A. The center-to-center spacing A is preferably at least four times of the side-to-side spacing B. Thus spaces 411 are formed between the sound-attenuating structures 410. These spaces 411 are relatively narrow in that the side-to-side spacing B is smaller than the length of the sound-attenuating structures 410. In particular the aspect ratio of the length of the sound-attenuating structures 410 relative to the side-to-side spacing B is at least 5:1.

The sound attenuator further 40 further comprises ribs 420 that protrude from the attenuator shell 41 between groups of sound-attenuating structures 410. The ribs 420 are arranged parallel to each other and such that groups of the ribs 420 intersect. Thus major spaces 421 are provided in the attenuator shell 41 by the ribs 420 in addition to the spaces 411 between the sound-attenuation structures 410.

By the spaces 411 and the major spaces 421 an attenuation effect is achieved that resembles that of a foamed attenuator although the sound attenuator 40 is nonporous and in particular foam-free.

Figure 4:
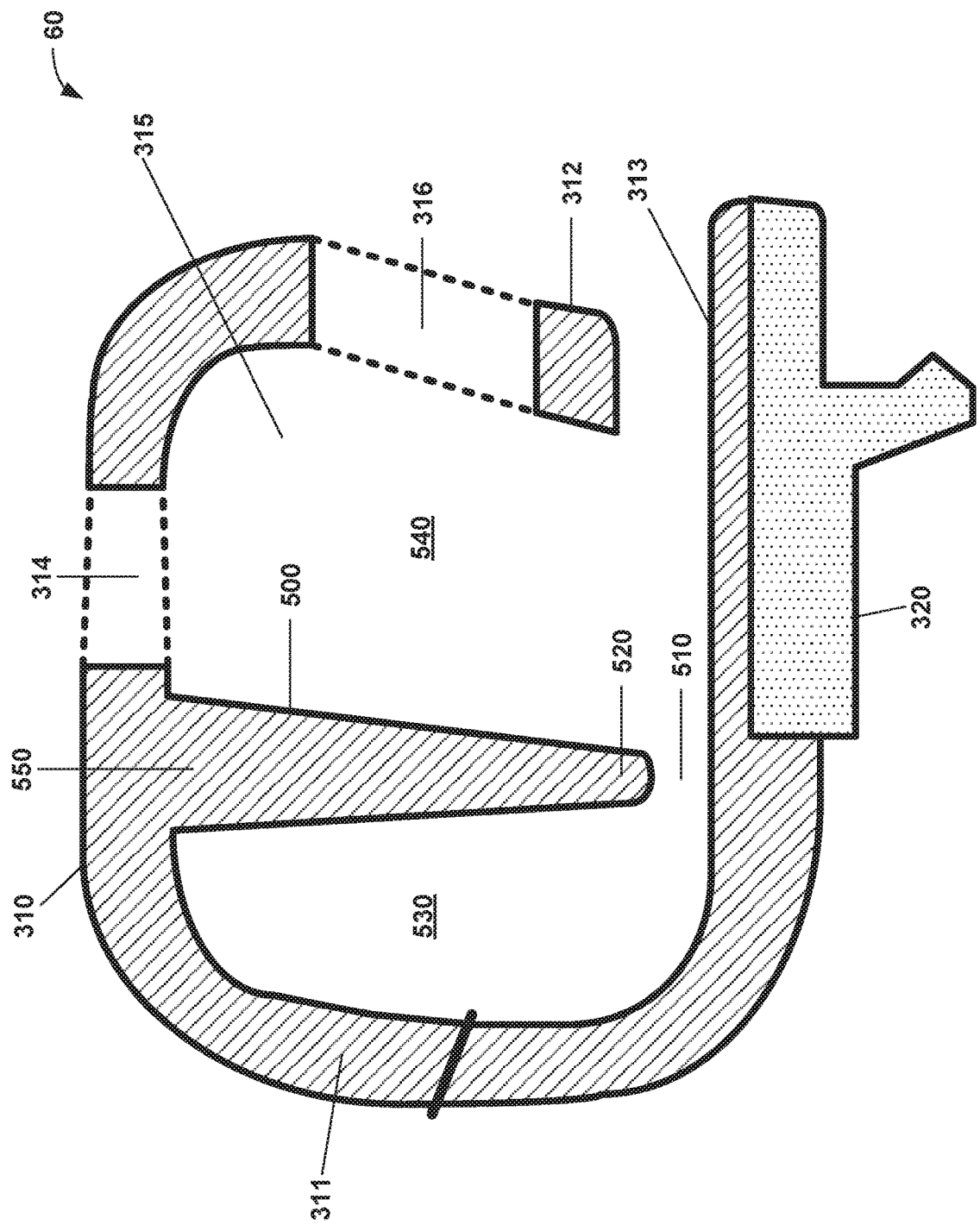
FIG. 4 is a cross sectional view of a cushion for a hearing protector according to an embodiment of the invention.

FIG. 4 shows a cross sectional view of a cushion 60 according to the invention. It is identical to the cushion 30 shown in FIG. 2, except that it has a resilient circumferential dividing wall 500 protruding from the contact pad 310 in a direction toward the attachment 320. The cushion 30 is shown in an uncompressed state, such as it would be when the hearing protector in which it may be comprised is not in use. In this state the dividing wall 500 provides a gap 510 between a free end 520 of the dividing wall 500 and the attachment flange 313. When the cushion 60 is compressed the gap 510 closes such that a closed volume 530 is formed between the dividing wall 500 and the sound insulation tube 311.

The dividing wall 500 is arranged in the chamber 315 circumferentially around the inner space and subdivides the chamber 315 into two coaxial ring-shaped compartments 530, 540, when the hearing protector is worn, with one compartment (the "inner compartment") 530 being closer to the sound insulation tube 311 and the other compartment (the "outer compartment") 540 being closer to the collar 312. The dividing wall 500 extends, in the chamber 315, from the contact pad 310 toward the attachment flange 313, essentially parallel to the sound insulation tube 311. The foot 550 of the dividing wall 500 is located on the contact pad 310 between the sound insulation tube 311 and the collar 312. The dividing wall 500 extends toward the attachment flange 313 far enough for its free end 520 to contact the attachment flange 313 when the hearing protector is worn, i.e. when there is pressure on the contact pad 310. The dividing wall 500 extends toward the attachment flange 313 only so far as its free end 520 to leave a gap 510 between the dividing wall 500 and the attachment flange 313 when the hearing protector is not worn, i.e. if there is no pressure on the contact pad 310.

Figure 5:
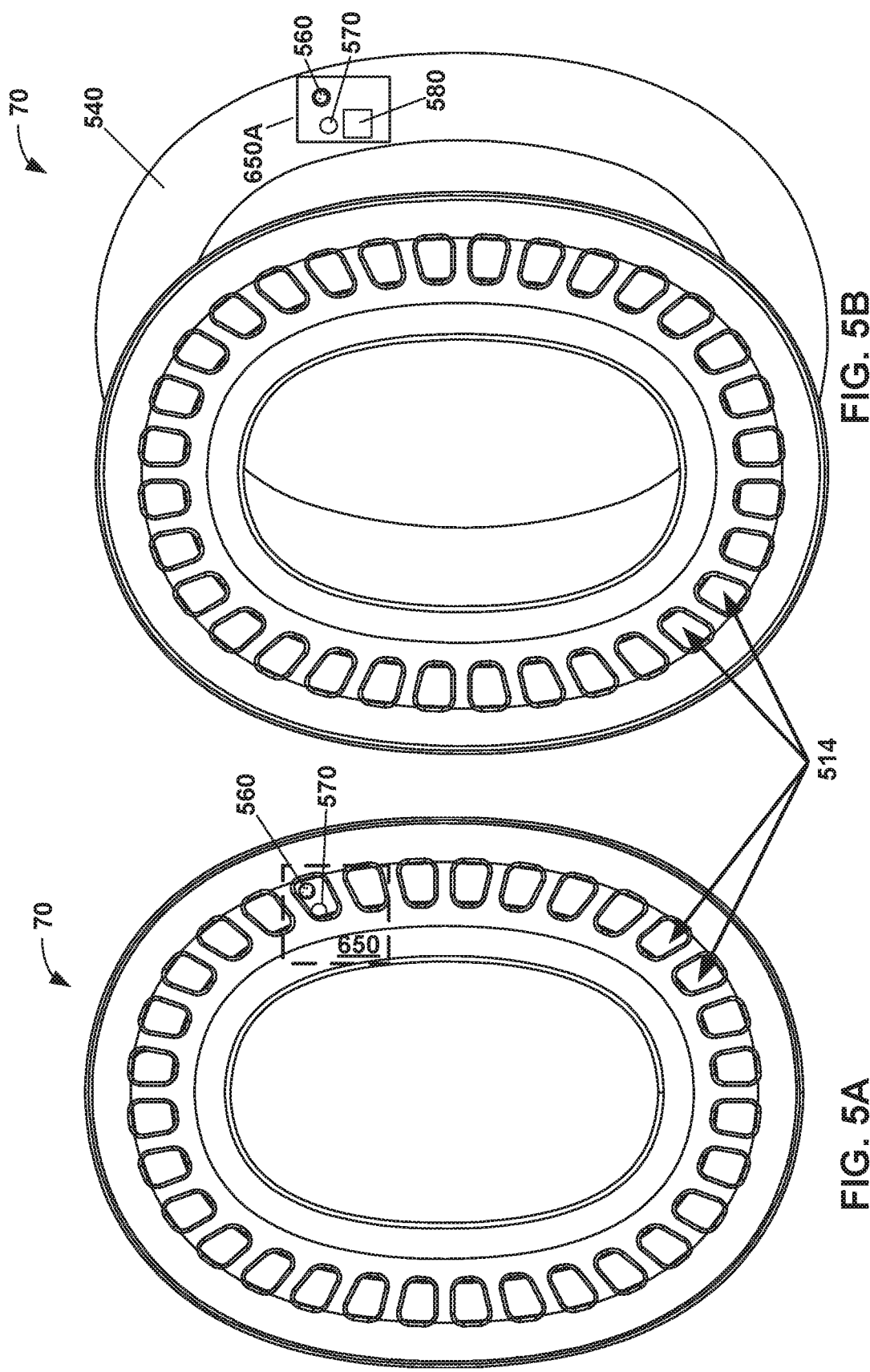
FIG. 5A is a perspective view of a cushion for a hearing protector with embedded physiological sensor according to an embodiment of the invention.
FIG. 5B is a partial exploded view of a hearing protector with embedded physiological sensor according to an embodiment of the invention.

FIG. 5A is a perspective view of a cushion for a hearing protector with one or more embedded physiological sensors, in accordance with some examples of this disclosure. Workers that have jobs in hot and/or stressful environments may be at risk of heat-related illnesses. Such workers may include firefighters, first responders, soldiers, construction workers, foundry workers and the like. Typically, such workers typically wear protective gear, such as personal protective equipment (PPE), which in some cases may further contribute to the heat and discomfort of the worker's body. Heat-related illnesses are a concern for such workers, and such illnesses can result in serious injury or even death.

Continuous monitoring of a worker's physiological condition may provide for early detection of signs of heat-related or other illness. Measuring core body temperature or calculating core body temperature from another parameter, such as breathing rate, heart rate or heart rate variability, may help prevent heat-related or other illness by allowing for early warning of potential catastrophic events. Early warning may provide sufficient time to engage in preventative measures, such as removing of the worker from the hot environment, providing hydration, and/or providing cooling measures. In addition to heat-related illness detection, it is beneficial to detect the general onset of health-adverse events for workers in stressful occupations, such as firefighters and military personnel. Therefore, there is potential value for an accurate, comfortable and unobtrusive device for individual physiological monitoring of workers.

In some examples in accordance with this disclosure, an effective means to monitor a worker's physiological condition includes incorporating one or more physiological monitoring sensors directly into personal protective equipment (PPE) already worn by the worker. In some examples, the incorporation of the physiological sensor does not result in worker discomfort, does not require modification of the PPE structure, and does not reduce the effectiveness of the PPE.

In the example depicted in FIG. 5A, a cushion 70 for an earmuff, such as earmuff 10 depicted in FIG. 1, includes a plurality of inlets 514 defining a ventilation passage or air channel between the skin of a wearer and the outside environment, such that sweat may evaporate off the skin and outward through the ventilation passage. In some examples, inlets 514 may be a non-limiting example of inlets 314 as shown in FIGS. 2 and 4. In addition to allowing for fluid communication with the outside environment, one or more of inlets 514 may simultaneously define at least partial line-of-sight between a physiological sensor 650 disposed within cushion 70 and the skin of a wearer, without further modification of the physical structure of the cushion 70.

In some examples, at least one physiological sensor 650 may be disposed within the ventilation passage that extends entirely through the cushion, wherein the physiological sensor is configured to generate signal data associated with one or more physiological parameters of the wearer.

Physiological sensor 650 may include any detection device configured to measure one or more values indicative of a physical condition of the human body. Sensor 650 may be configured to detect and/or measure, for example, a pulse rate, oxygen saturation, breathing rate, brain electrical activity, body temperature, perspiration, hydration, or any other bodily condition. Although sensor 650 is depicted near the upper-right corner of earmuff cushion 70 in FIG. 5A, sensor 650 may be located anywhere within the circumference of cushion 70.

In some examples, physiological sensor 650 may include components configured to monitor a wearer's pulse rate and/or blood oxygen saturation ($SO_2$) (e.g., peripheral oxygen saturation, $SpO_2$) via pulse oximetry. Pulse oximetry includes the measurement of light absorbance using a method known as photoplethysmography (PPG). Pulse oximetry through light absorbance is calculated from red and near infrared light transmission or reflection through skin and tissue, which in turn can be used to determine the pulse rate and pulse rate variation. The PPG signal oscillates due to change in blood volume with each heartbeat, thereby measuring the pulse. Pulse measurements may be used as a proxy to determine core body temperature. For example, an increased heart rate may indicate an increased core body temperature, at a rate of increase of approximately 10 BPM for every 1 degree Celsius of increased body temperature.

In some examples, physiological sensor 650 may include a PPG device disposed within earmuff cushion 70. Sensor 650 may include a light emitter 560 configured to emit a beam of light outward through inlet 514 and toward the skin of a wearer.

In some examples, a PPG sensor (for example, an $SpO_2$ sensor) may be located within one of inlets 514 such that light emitter 560 emits a beam of light emitted toward a temporal artery of the wearer, for example, along the front of the ear. In this configuration, the sensor may receive a strong signal from the artery, although it may be subject to noise from jaw movement, such as via talking by the wearer.

In some examples, a PPG sensor (for example, an $SpO_2$ sensor) may be located within one of inlets 514 such that light emitter 560 emits a beam of light toward the skull behind an ear of the wearer. In this configuration, the sensor may receive a weaker signal from the artery, although it may be less subject to noise.

In some examples, cushion 70 may include multiple PPG sensors (for example, $SpO_2$ sensors) each sensor disposed within one of inlets 514 such that light emitters 560 emit beams of light toward different regions of the head of the wearer. In this configuration, processing circuitry may evaluate a relative signal quality of each sensor and select from among them, or alternatively, average the signals from multiple sensors to identify and factor out noise in the combined signal.

FIG. 5B is a partial exploded view of a hearing protector with embedded physiological sensor in accordance with some examples of this disclosure. In the example depicted in FIG. 5B, a cushion 70 for an earmuff, such as earmuff 10 depicted in FIG. 1, includes a plurality of inlets 514 defining a ventilation passage or air channel between the skin of a wearer and the outside environment, such that sweat may evaporate off the skin and outward through the ventilation passage. In addition to allowing for fluid communication with the outside environment, one or more of inlets 514 may simultaneously define at least partial line-of-sight between a physiological sensor 650 disposed within internal cavity 540 of cushion 70 and the skin of a wearer, without further modification of the physical structure of the cushion 70.

In some examples, at least one physiological sensor 650 may be disposed within the ventilation passage that extends entirely through the cushion, wherein the at least one physiological sensor is configured to generate signal data associated with one or more physiological parameters of the wearer. Although FIG. 5B depicts a single physiological sensor 650A, earmuff cushion 70 may include any number of physiological sensors (e.g. 650B, 650C, etc.).

Physiological sensor 650 may include any detection device configured to measure one or more values indicative of a physical condition of the human body. Sensor 650 may be configured to detect and/or measure, for example, a pulse rate, oxygen saturation, breathing rate, brain electrical activity, body temperature, perspiration, hydration, or any other bodily condition.

In some examples, physiological sensor 650 may include components configured to monitor a wearer's pulse rate and/or blood oxygen saturation ($SO_2$) (e.g., peripheral oxygen saturation, $SpO_2$) via pulse oximetry. Pulse oximetry includes the measurement of light absorbance using a method known as photoplethysmography (PPG). Pulse oximetry through light absorbance is calculated from red and near infrared light transmission or reflection through skin and tissue, which in turn can be used to determine the pulse rate and pulse rate variation. The PPG signal oscillates due to change in blood volume with each heartbeat, thereby measuring the pulse. Pulse measurements may be used as a proxy to determine core body temperature. For example, an increased heart rate may indicate an increased core body temperature, at a rate of increase of approximately 10 BPM for every 1 degree Celsius of increased body temperature.

In some examples, physiological sensor 650 may include a PPG device disposed within internal cavity 540 of earmuff cushion 70. Sensor 650 may include light emitter 560, configured to emit a beam of light outward through inlet 514 and toward the skin of a wearer. Sensor 650 may further include a light detector 570, configured to detect light reflected off of the wearer's skin and back through inlet 514. In other examples, cushion 70 may be composed of a material that is substantially transparent to the beam of light, and light emitter 560 may be positioned behind the material, rather than within inlet 514.

In some examples, sensor 650 may further include processing circuitry 580 configured to receive raw electrical signals from light detector 570 and convert them to data indicative of light absorbance, further indicative of the wearer's pulse oximetry. In some examples, data processing may occur locally within processing circuitry 580 of sensor 650. In other examples, sensor 650 may include a transmitter to communicate (e.g., wirelessly) with a remote computing system (e.g. cloud-based computing device, mobile device, data-logging device, heads-up display, fusion hub, etc.) to further process data from sensor 650. In other examples, sensor 650 may include a transmitter to communicate (e.g., wirelessly) with processing circuitry 580 housed locally within the earmuff.

In some examples, sensor 650 includes a battery disposed inside internal cavity 540 of cushion 70. In other examples, earmuff 10 as shown in FIG. 1 may include one-way or two-way communication capability (e.g., radio, walkie-talkie, etc.) having a power source, wherein sensor 650 may be configured to share electrical power from the power source of the communication device.

In some examples, processing circuitry 580, either local to sensor 650 and/or the earmuff, or cloud-based, may process data from sensor 650 to determine core pulse, blood oxygen saturation, or core body temperature of a wearer as an indication of the wearer's general physiological condition. For example, processing circuitry 580 may determine a specific blood oximetry measurement indicating a pulse that is at or above a predetermined threshold, indicative of a relative level of distress, or a significant probability of an adverse physiological condition, such as a heat-related illness (e.g., dehydration, excessive body temperature, etc.).

In some examples, processing circuitry 580 may be configured to output an indication, for example, an alert or alarm, of a sensor measurement at or above a predetermined threshold level. For example, earmuff 10 of FIG. 1 may include communication means, including speakers. Sensor 650 may include means to output an audio alert through speakers, informing the wearer of an unsafe pulse, core body temperature, or other physiologically distressed condition. In some examples, processing circuitry 580 may output a visual or text-based alert to a computing device, such as a mobile device held by the wearer himself and/or a designated safety supervisor, informing them of a high probability of a significant physiological condition. In another example, sensor 650 may include a haptic feedback device to indicate to the wearer via a vibration sensation, that the worker's health may be at risk in its current state.

Figure 6:
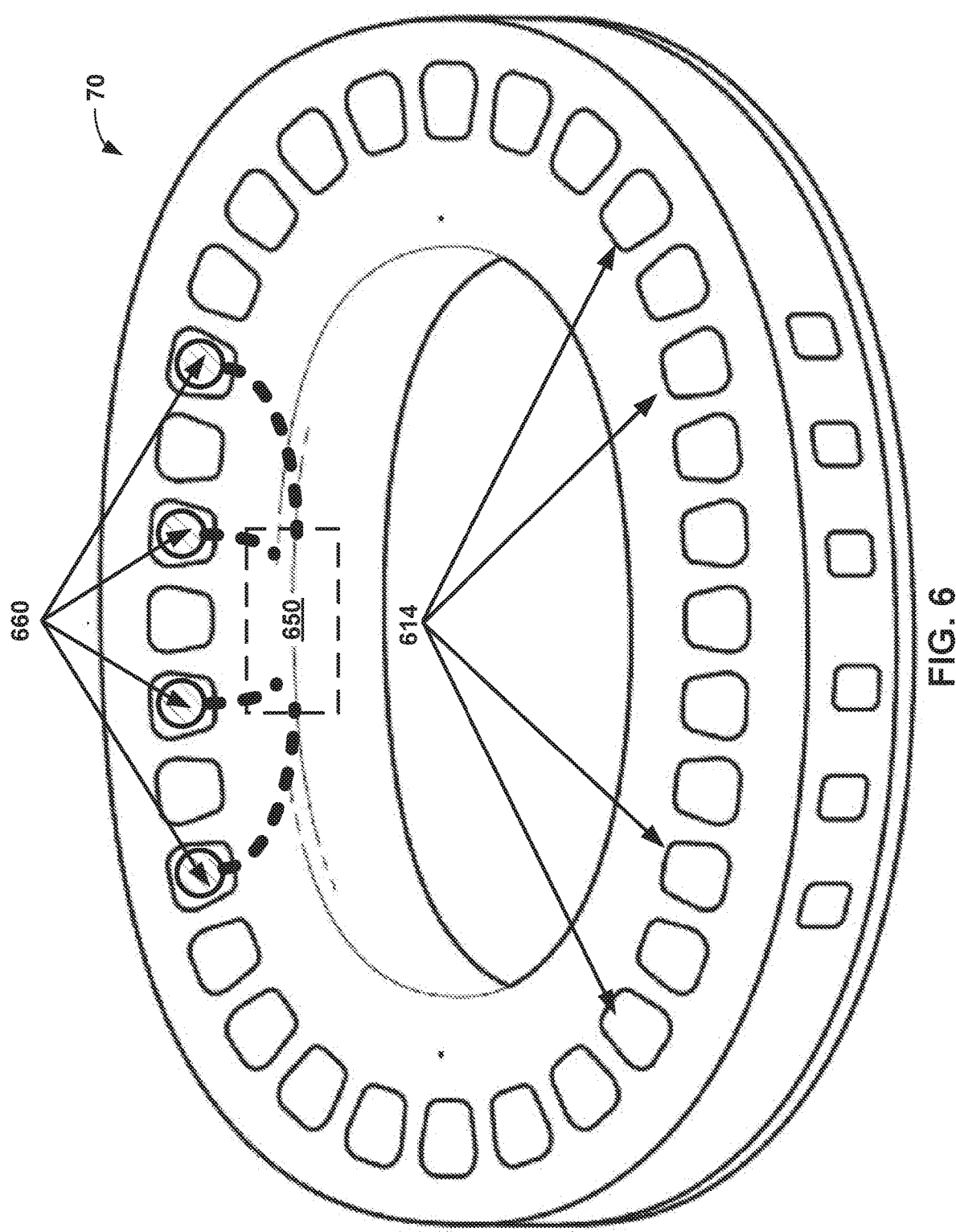
FIG. 6 is a perspective view of a cushion for a hearing protector with embedded physiological sensor according to an embodiment of the invention.

FIG. 6 is a perspective view of a cushion for a hearing protector with one or more embedded physiological sensors, according to an embodiment of the invention. Fatigue, drowsiness, and momentary loss of awareness on the worksite can, in some cases, be blamed for reduced productivity, poor work product, and accidents constituting safety hazards, especially if resulting from a seizure. Therefore, there may be potential benefits in monitoring worker alertness and fatigue and providing an alerting signal when fatigue or drowsiness is detected. One method to monitor worker fatigue is by measuring electroencephalogram (EEG) waveforms, also known as brain waves. For example, a state of fatigue may be directly inferred from a known pattern of EEG waveforms. In another example, a state of fatigue may be indirectly inferred from a pattern of EEG waveforms that more directly indicates excessive blinking of the eyes.

EEG waveforms are typically measured using an array of electrodes applied to a headpiece secured to the scalp. The metal electrodes typically have intimate contact with the skin in order to collect accurate measurements. Part of the array of electrodes may be additionally used for the measurement of electrodermal activity (EDA) in form of impedance, resistance or conductance of the skin across multiple electrodes. EDA, in addition to EEG, provides information about sweat and potential exertion of the wearer and related sympathetic activity of the nervous system, and supplements information from the other sensors for determining a high probability of an adverse physiological condition.

In some examples in accordance with this disclosure, and as described in association with certain examples above, an effective means to monitor a worker's physiological condition includes incorporating one or more physiological monitoring sensors directly into personal protective equipment (PPE) already worn by the worker. In some examples, the incorporation of the physiological sensor does not result in worker discomfort, does not require modification of the PPE structure, and does not reduce the effectiveness of the PPE.

In the example depicted in FIG. 6, a cushion 70 for an earmuff, such as earmuff 10 depicted in FIG. 1, includes a plurality of inlets 614 defining a ventilation passage or air channel between the skin of a wearer and the outside environment, such that sweat may evaporate off the skin and outward through the ventilation passage. In some examples, inlets 614 may be a non-limiting example of inlets 314 as shown in FIGS. 2 and 4. In addition to allowing for fluid communication with the outside environment, one or more of inlets 614 may simultaneously define a passage between a physiological sensor 650 disposed within cushion 70 and the skin of a wearer, without further modification of the physical structure of the cushion 70.

Physiological sensor 650 may include any detection device configured to measure one or more values indicative of a physical condition of the human body. Sensor 650 may be configured to detect and/or measure, for example, a pulse rate, oxygen saturation, breathing rate, brain electrical activity, body temperature, perspiration, hydration, or any other bodily condition.

In some examples in accordance with this disclosure, earmuff cushion 70 includes a physiological sensor 650 configured to monitor a wearer's fatigue. For example, sensor 650 may be configured to measure EEG waveforms, also known as brain waves, to monitor worker fatigue. In some examples, sensor 650 includes an array of EEG electrodes 660 disposed within inlets 614, near the outer surface of cushion 70 such that they may contact the skin when the earmuff is placed over the ear of a wearer. Electrodes 660 typically have intimate contact with the skin in order to collect accurate measurements. In addition to the scalp, another location that provides good brain wave signal is behind the ear—the area behind the ears is typically free of hair and fat tissue making it ideal for extracting electrical signals. In the non-limiting example of FIG. 6, earmuff cushion 70 incorporates four electrodes 660 allowing for intimate contact with the skin behind the ears. In other examples, earmuff cushion 70 may include fewer or more than four electrodes. In some examples, cushion 70 may simultaneously include multiple different types of sensors, including both a PPG sensor and an EEG sensor. In some examples, cushion 70 may be composed of a material that is substantially electrically conductive, and electrodes 660 may be incorporated within or behind the material, rather than within inlets 614.

In some examples, sensor 650 may further include processing circuitry 580 configured to receive raw electrical signals from electrodes 660 and convert them to data indicative of electrical activity within the wearer's brain, further indicative of the wearer's fatigue. In some examples, data processing may occur locally within processing circuitry 580 of sensor 650. In other examples, sensor 650 may include a transmitter to communicate (e.g., wirelessly) with a remote computing system (e.g., cloud-based computing device, mobile device, data-logging device, heads-up display, fusion hub, etc.) to further process data from sensor 650. In other examples, sensor 650 may include a transmitter to communicate (e.g., wirelessly) with processing circuitry 580 housed locally within the earmuff.

In some examples, sensor 650 includes a battery disposed inside internal cavity 540 of cushion 70. In other examples, earmuff 10 as shown in FIG. 1 may include one-way or two-way communication capability (e.g., radio, walkie-talkie, etc.) having a power source, wherein sensor 650 may be configured to share electrical power from the power source of the communication device.

In some examples, processing circuitry 580, either local to sensor 650 and/or the earmuff, or cloud-based, may process data from sensor 650 to determine fatigue of a wearer. For example, processing circuitry 580 may determine a specific measurement of electrical activity within the brain indicative of a probability (e.g., significant probability) of an adverse physiological condition of the wearer, such as general fatigue, drowsiness, or loss of consciousness.

In some examples, processing circuitry 580 may be configured to output an indication, for example, an alert or alarm, of a sensor measurement at or above a predetermined threshold level. For example, earmuff 10 of FIG. 1 may include communication means, including speakers. Sensor 650 may include means to output an audio alert through speakers, informing the wearer of an unsafe pulse, core body temperature, or other physiologically distressed condition. In some examples, processing circuitry 580 may output a visual or text-based alert to a computing device, such as a mobile device held by the wearer himself and/or a designated safety supervisor, informing them of a high probability of a significant physiological condition, and allowing the safety officer to recommend a break for the worker or to assign the worker a less-demanding task. In another example, sensor 650 may include a haptic feedback device to indicate to the wearer via a vibration sensation, that the worker's health may be at risk in its current state.

Figure 7:
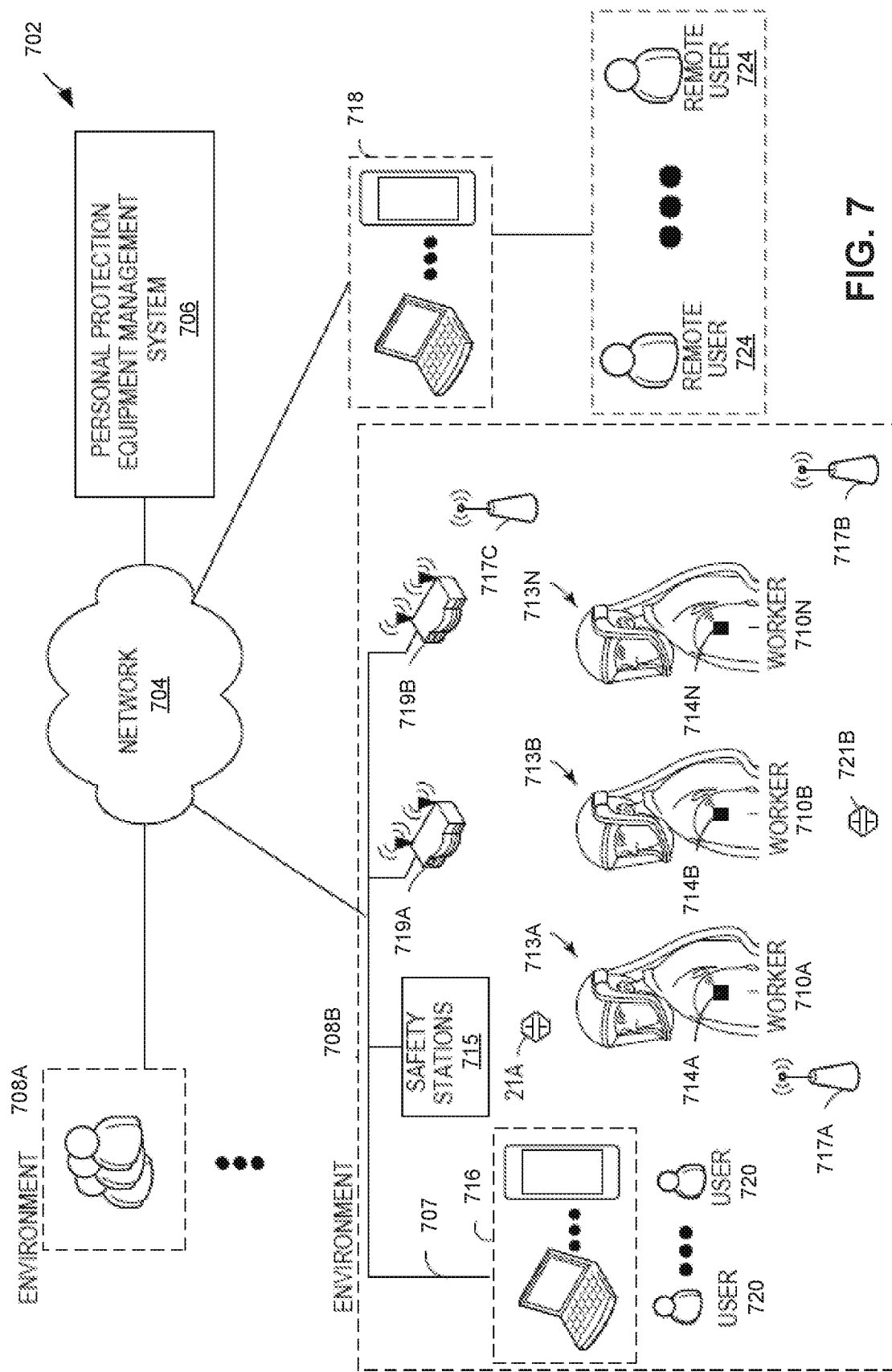
FIG. 7 is a block diagram illustrating an example system in which personal protection equipment (PPEs), such as filtered air respirator systems and ear muffs having embedded sensors and communication capabilities, are utilized within a number of work environments and are managed by a personal protection equipment management system (PPEMS) in accordance with various techniques of this disclosure.

FIG. 7 is a block diagram illustrating an example computing system 702 that includes a personal protection equipment management system (PPEMS) 706 for managing personal protection equipment. As described herein, PPEMS allows authorized users to perform preventive occupational health and safety actions and manage inspections and maintenance of safety protective equipment. By interacting with PPEMS 706, safety professionals can, for example, manage area inspections, worker inspections, worker health and safety compliance training.

In general, PPEMS 706 provides data acquisition, monitoring, activity logging, reporting, predictive analytics, PPE control, and alert generation. For example, PPEMS 706 includes an underlying analytics and safety event prediction engine and alerting system in accordance with various examples described herein. In general, a safety event may refer to activities of a user of personal protective equipment (PPE), a condition of the PPE, or an environmental condition (e.g., which may be hazardous). In some examples, a safety event may be an injury or worker condition, workplace harm, or regulatory violation. For example, in the context of fall protection equipment, a safety event may be misuse of the fall protection equipment, a user of the fall equipment experiencing a fall, or a failure of the fall protection equipment. In the context of a respirator, a safety event may be misuse of the respirator, a user of the respirator not receiving an appropriate quality and/or quantity of air, or failure of the respirator. A safety event may also be associated with a hazard in the environment in which the PPE is located. In some examples, occurrence of a safety event associated with the article of PPE may include a safety event in the environment in which the PPE is used or a safety event associated with a worker using the article of PPE. In some examples, a safety event may be an indication that PPE, a worker, and/or a worker environment are operating, in use, or acting in a way that is normal operation, where normal operation is a predetermined or predefined condition of acceptable or safe operation, use, or activity. In some examples, a safety event may be an indication of an unsafety condition, wherein the unsafe condition represents a state outside of a set of defined thresholds, rules, or other limits configured by a human operator and/or are machine-generated.

Examples of PPE include, but are not limited to respiratory protection equipment (including disposable respirators, reusable respirators, powered air purifying respirators, and supplied air respirators), protective eyewear, such as visors, goggles, filters or shields (any of which may include augmented reality functionality), protective headwear, such as hard hats, hoods or helmets, hearing protection (including ear plugs and ear muffs), protective shoes, protective gloves, other protective clothing, such as coveralls and aprons, protective articles, such as sensors, safety tools, detectors, global positioning devices, mining cap lamps, fall protection harnesses, exoskeletons, self-retracting lifelines, heating and cooling systems, gas detectors, and any other suitable gear. In some examples, a data hub, such as data 714N may be an article of PPE.

As further described below, PPEMS 706 provides an integrated suite of personal safety protection equipment management tools and implements various techniques of this disclosure. That is, PPEMS 706 provides an integrated, end-to-end system for managing personal protection equipment, e.g., safety equipment, used by workers 710 within one or more physical environments 708, which may be construction sites, mining or manufacturing sites or any physical environment. The techniques of this disclosure may be realized within various parts of computing environment 702.

As shown in the example of FIG. 7, system 702 represents a computing environment in which a computing device within of a plurality of physical environments 708A, 708B (collectively, environments 708) electronically communicate with PPEMS 706 via one or more computer networks 704. Each of physical environment 708 represents a physical environment, such as a work environment, in which one or more individuals, such as workers 710, utilize personal protection equipment while engaging in tasks or activities within the respective environment.

In this example, environment 708A is shown as generally as having workers 710, while environment 708B is shown in expanded form to provide a more detailed example. In the example of FIG. 7, a plurality of workers 710A-710N are shown as utilizing respective respirators 713A-713N.

As further described herein, each of respirators 713 includes embedded sensors or monitoring devices and processing electronics configured to capture data in real-time as a user (e.g., worker) engages in activities while wearing the respirators. For example, as described in greater detail herein, respirators 713 may include a number of components (e.g., a head top, a blower, a filter, and the like) respirators 713 may include a number of sensors for sensing or controlling the operation of such components. A head top may include, as examples, a head top visor position sensor, a head top temperature sensor, a head top motion sensor, a head top impact detection sensor, a head top position sensor, a head top battery level sensor, a head top head detection sensor, an ambient noise sensor, or the like. A blower may include, as examples, a blower state sensor, a blower pressure sensor, a blower run time sensor, a blower temperature sensor, a blower battery sensor, a blower motion sensor, a blower impact detection sensor, a blower position sensor, or the like. A filter may include, as examples, a filter presence sensor, a filter type sensor, or the like. Each of the above-noted sensors may generate usage data, as described herein.

In addition, each of respirators 713 may include one or more output devices for outputting data that is indicative of operation of respirators 713 and/or generating and outputting communications to the respective worker 710. For example, respirators 713 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback).

In general, each of environments 708 include computing facilities (e.g., a local area network) by which respirators 713 are able to communicate with PPEMS 706. For example, environments 708 may be configured with wireless technology, such as 802.11 wireless networks, 802.15 ZigBee networks, and the like. In the example of FIG. 7, environment 708B includes a local network 707 that provides a packet-based transport medium for communicating with PPEMS 706 via network 704. In addition, environment 708B includes a plurality of wireless access points 719A, 719B that may be geographically distributed throughout the environment to provide support for wireless communications throughout the work environment.

Each of respirators 713 is configured to communicate data, such as sensed motions, events and conditions, via wireless communications, such as via 802.11 Wi-Fi protocols, Bluetooth protocol or the like. Respirators 713 may, for example, communicate directly with a wireless access point 719. As another example, each worker 710 may be equipped with a respective one of wearable communication hubs 714A-714M that enable and facilitate communication between respirators 713 and PPEMS 706. For example, respirators 713 as well as other PPEs (such as fall protection equipment, hearing protection, hardhats, or other equipment) for the respective worker 710 may communicate with a respective communication hub 714 via Bluetooth or other short range protocol, and the communication hubs may communicate with PPEMs 706 via wireless communications processed by wireless access points 719. Although shown as wearable devices, hubs 714 may be implemented as stand-alone devices deployed within environment 8B. In some examples, hubs 714 may be articles of PPE. In some examples, communication hubs 714 may be an intrinsically safe computing device, smartphone, wrist- or head-wearable computing device, or any other computing device.

In general, each of hubs 714 operates as a wireless device for respirators 713 relaying communications to and from respirators 713, and may be capable of buffering usage data in case communication is lost with PPEMS 706. Moreover, each of hubs 714 is programmable via PPEMS 706 so that local alert rules may be installed and executed without requiring a connection to the cloud. As such, each of hubs 714 provides a relay of streams of usage data from respirators 713 and/or other PPEs within the respective environment, and provides a local computing environment for localized alerting based on streams of events in the event communication with PPEMS 706 is lost.

As shown in the example of FIG. 7, an environment, such as environment 708B, may also include one or more wireless-enabled beacons, such as beacons 717A-7170, that provide accurate location information within the work environment. For example, beacons 717A-717C may be GPS-enabled such that a controller within the respective beacon may be able to precisely determine the position of the respective beacon. Based on wireless communications with one or more of beacons 717, a given respirator 713 or communication hub 714 worn by a worker 710 is configured to determine the location of the worker within work environment 78B. In this way, event data (e.g., usage data) reported to PPEMS 706 may be stamped with positional information to aid analysis, reporting and analytics performed by the PPEMS.

In addition, an environment, such as environment 708B, may also include one or more wireless-enabled sensing stations, such as sensing stations 721A, 721B. Each sensing station 721 includes one or more sensors and a controller configured to output data indicative of sensed environmental conditions. Moreover, sensing stations 721 may be positioned within respective geographic regions of environment 708B or otherwise interact with beacons 717 to determine respective positions and include such positional information when reporting environmental data to PPEMS 706. As such, PPEMS 706 may be configured to correlate the sense environmental conditions with the particular regions and, therefore, may utilize the captured environmental data when processing event data received from respirators 713. For example, PPEMS 706 may utilize the environmental data to aid generating alerts or other instructions for respirators 713 and for performing predictive analytics, such as determining any correlations between certain environmental conditions (e.g., heat, humidity, visibility) with abnormal worker behavior or increased safety events. As such, PPEMS 706 may utilize current environmental conditions to aid prediction and avoidance of imminent safety events. Example environmental conditions that may be sensed by sensing stations 721 include but are not limited to temperature, humidity, presence of gas, pressure, visibility, wind and the like.

In example implementations, an environment, such as environment 708B, may also include one or more safety stations 715 distributed throughout the environment to provide viewing stations for accessing respirators 713. Safety stations 715 may allow one of workers 710 to check out respirators 713 and/or other safety equipment, verify that safety equipment is appropriate for a particular one of environments 708, and/or exchange data. For example, safety stations 715 may transmit alert rules, software updates, or firmware updates to respirators 713 or other equipment. Safety stations 715 may also receive data cached on respirators 713, hubs 714, and/or other safety equipment. That is, while respirators 713 (and/or data hubs 714) may typically transmit usage data from sensors of respirators 713 to network 704 in real time or near real time, in some instances, respirators 713 (and/or data hubs 714) may not have connectivity to network 704. In such instances, respirators 713 (and/or data hubs 714) may store usage data locally and transmit the usage data to safety stations 715 upon being in proximity with safety stations 715. Safety stations 715 may then upload the data from respirators 713 and connect to network 704.

In addition, each of environments 708 include computing facilities that provide an operating environment for end-user computing devices 716 for interacting with PPEMS 706 via network 704. For example, each of environments 708 typically includes one or more safety managers responsible for overseeing safety compliance within the environment. In general, each user 720 interacts with computing devices 716 to access PPEMS 706. Each of environments 708 may include systems. Similarly, remote users may use computing devices 718 to interact with PPEMS via network 704. For purposes of example, the end-user computing devices 716 may be laptops, desktop computers, mobile devices such as tablets or so-called smart phones and the like.

Users 720, 724 interact with PPEMS 706 to control and actively manage many aspects of safely equipment utilized by workers 710, such as accessing and viewing usage records, analytics and reporting. For example, users 720, 724 may review usage information acquired and stored by PPEMS 706, where the usage information may include data specifying starting and ending times over a time duration (e.g., a day, a week, or the like), data collected during particular events, such as lifts of a visor of respirators 713, removal of respirators 713 from a head of workers 710, changes to operating parameters of respirators 713, status changes to components of respirators 713 (e.g., a low battery event), motion of workers 710, detected impacts to respirators 713 or hubs 714, sensed data acquired from the user, environment data, and the like. In addition, users 720, 724 may interact with PPEMS 706 to perform asset tracking and to schedule maintenance events for individual pieces of safety equipment, e.g., respirators 713, to ensure compliance with any procedures or regulations. PPEMS 706 may allow users 720, 724 to create and complete digital checklists with respect to the maintenance procedures and to synchronize any results of the procedures from computing devices 716, 718 to PPEMS 706.

Further, as described herein, PPEMS 706 integrates an event processing platform configured to process thousand or even millions of concurrent streams of events from digitally enabled PPEs, such as respirators 713. An underlying analytics engine of PPEMS 706 applies historical data and models to the inbound streams to compute assertions, such as identified anomalies or predicted occurrences of safety events based on conditions or behavior patterns of workers 710. Further, PPEMS 706 provides real-time alerting and reporting to notify workers 710 and/or users 720, 724 of any predicted events, anomalies, trends, and the like.

The analytics engine of PPEMS 706 may, in some examples, apply analytics to identify relationships or correlations between sensed worker data, environmental conditions, geographic regions and other factors and analyze the impact on safety events. PPEMS 706 may determine, based on the data acquired across populations of workers 710, which particular activities, possibly within certain geographic region, lead to, or are predicted to lead to, unusually high occurrences of safety events.

In this way, PPEMS 706 tightly integrates comprehensive tools for managing personal protection equipment with an underlying analytics engine and communication system to provide data acquisition, monitoring, activity logging, reporting, behavior analytics and alert generation. Moreover, PPEMS 706 provides a communication system for operation and utilization by and between the various elements of system 702. Users 720, 724 may access PPEMS 706 to view results on any analytics performed by PPEMS 706 on data acquired from workers 710. In some examples, PPEMS 706 may present a web-based interface via a web server (e.g., an HTTP server) or client-side applications may be deployed for devices of computing devices 716, 718 used by users 720, 724, such as desktop computers, laptop computers, mobile devices such as smartphones and tablets, or the like.

In some examples, PPEMS 706 may provide a database query engine for directly querying PPEMS 706 to view acquired safety information, compliance information and any results of the analytic engine, e.g., by the way of dashboards, alert notifications, reports and the like. That is, users 724, 726, or software executing on computing devices 716, 718, may submit queries to PPEMS 706 and receive data corresponding to the queries for presentation in the form of one or more reports or dashboards. Such dashboards may provide various insights regarding system 702, such as baseline ("normal") operation across worker populations, identifications of any anomalous workers engaging in abnormal activities that may potentially expose the worker to risks, identifications of any geographic regions within environments 702 for which unusually anomalous (e.g., high) safety events have been or are predicted to occur, identifications of any of environments 702 exhibiting anomalous occurrences of safety events relative to other environments, and the like.

As illustrated in detail below, PPEMS 706 may simplify workflows for individuals charged with monitoring and ensure safety compliance for an entity or environment. That is, the techniques of this disclosure may enable active safety management and allow an organization to take preventative or correction actions with respect to certain regions within environments 708, particular pieces of safety equipment or individual workers 710, define and may further allow the entity to implement workflow procedures that are data-driven by an underlying analytical engine.

As one example, the underlying analytical engine of PPEMS 706 may be configured to compute and present customer-defined metrics for worker populations within a given environment 708 or across multiple environments for an organization as a whole. For example, PPEMS 706 may be configured to acquire data and provide aggregated performance metrics and predicted behavior analytics across a worker population (e.g., across workers 710 of either or both of environments 708A, 708B). Furthermore, users 720, 724 may set benchmarks for occurrence of any safety incidences, and PPEMS 706 may track actual performance metrics relative to the benchmarks for individuals or defined worker populations.

As another example, PPEMS 706 may further trigger an alert if certain combinations of conditions are present, e.g., to accelerate examination or service of a safety equipment, such as one of respirators 713. In this manner, PPEMS 6 may identify individual respirators 713 or workers 710 for which the metrics do not meet the benchmarks and prompt the users to intervene and/or perform procedures to improve the metrics relative to the benchmarks, thereby ensuring compliance and actively managing safety for workers 710.

In some examples in accordance with this disclosure, a system 702 may include various components configured to allow safety professionals to manage area inspections, worker inspections, worker health and safety compliance training. For example, a system may include one or more computing devices configured to process and analyze data generated by one or more sensors embedded within an article of personal protective equipment.

In the example depicted in FIG. 7, PPEMS 706 may include processing circuitry, such as processing circuitry 580 depicted in FIG. 5B, configured to receive data indicative of an individual's physiological condition. In FIG. 7, each of workers 710 is depicted wearing an article of personal protective equipment (PPE) 713. Although FIG. 7 depicts PPE 713 as respiratory protection, PPE 713 could also include hearing protection, for example earmuffs 10 as shown in FIG. 1. PPE 713 may include one more embedded sensors, such as physiological sensor 650 depicted in FIGS. 5A, 5B, and 6, configured to receive signals from the body of worker 710. In some examples, PPE 713 may include a photoplethysmograph sensor and/or other optical sensor configured to determine the blood oximetry and other biomarkers of worker 710. In other examples, PPE 713 may include an EEG and/or EDA sensor and one or more electrodes configured to monitor the brain activity and/or electrodermal activity of worker 710.

In some examples, PPE 713 may include processing circuitry configured to analyze data from a physiological sensor. In other examples, PPE 713 may include transmission means, such as data communication hub 714, configured to transmit data from the physiological sensor, through network 704, and into processing circuitry within PPEMS 706, to determine a probability of a significant physiological condition.

Upon determination of a significant physiological condition, such as determining a threshold data measurement, processing circuitry, either local to a physiological sensor itself within PPE 713, or within PPEMS 706 may be configured to generate and output an alert. The alert may be sent to worker 710 via PPE 713, such as via audio, visual, or haptic feedback. In other examples, the alert may be sent to a mobile device 716 or 718. Mobile device 716, such as a pager, mobile phone, or personal computing device, may be held or accessed by worker 710. Mobile device 718, such as a pager, mobile phone, or personal computing device, may be held by remote user 724, such as a workplace safety supervisor, so that he may activate additional safety protocols to protect the health of worker 710.

Figure 8:
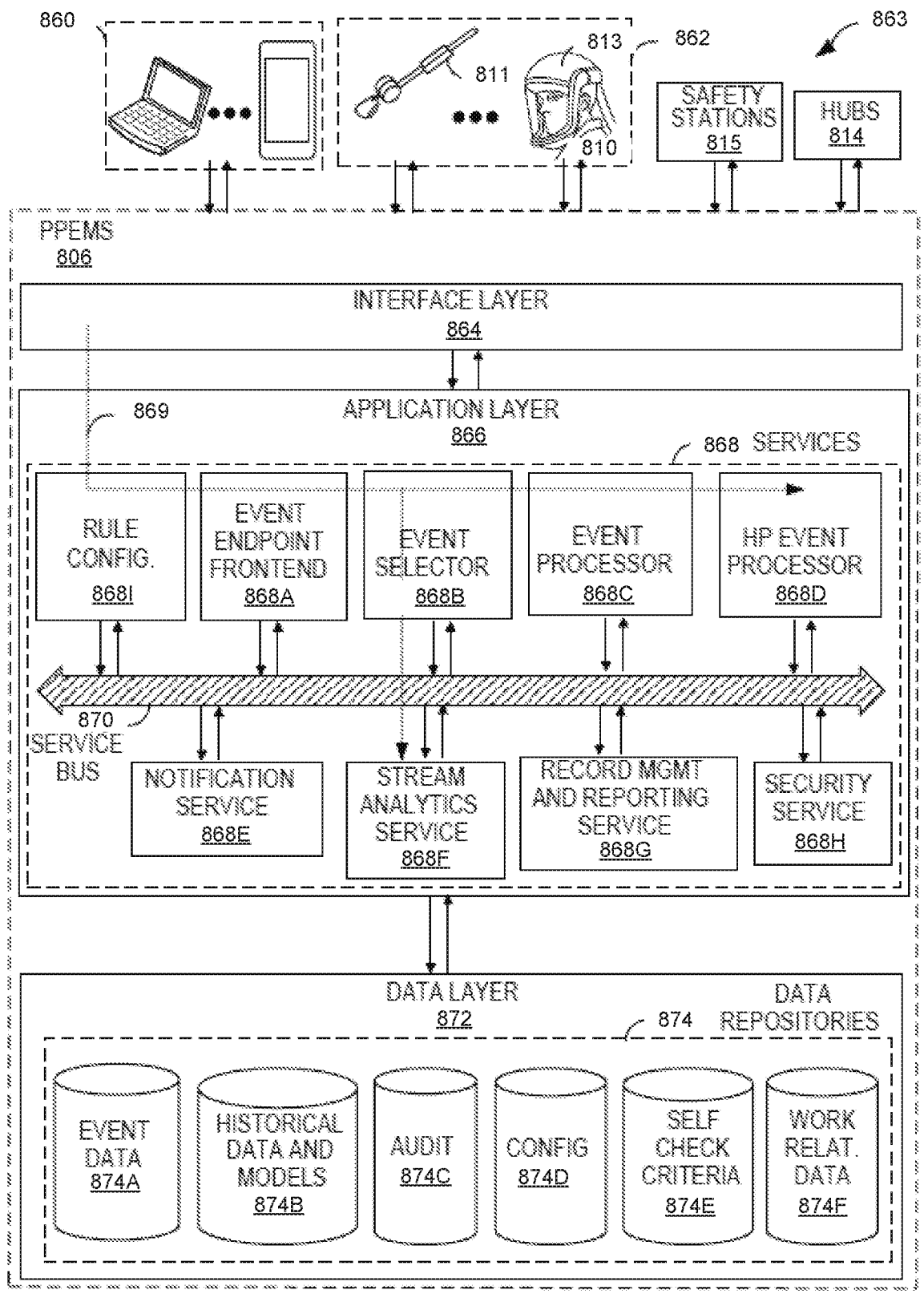
FIG. 8 is a block diagram illustrating an operating perspective of the personal protection equipment management system shown in FIG. 7 in accordance with various techniques of this disclosure.

FIG. 8 is a block diagram providing an operating perspective of PPEMS 806 when hosted as cloud-based platform capable of supporting multiple, distinct work environments 808 having an overall population of workers 810 that have a variety of communication enabled personal protection equipment (PPE), such as safety release lines (SRLs) 811, respirators 813, safety helmets, hearing protection or other safety equipment. In the example of FIG. 8, the components of PPEMS 806 are arranged according to multiple logical layers that implement the techniques of the disclosure. Each layer may be implemented by a one or more modules comprised of hardware, software, or a combination of hardware and software.

In FIG. 8, personal protection equipment (PPEs) 862, such as SRLs 811, respirators 813 and/or other equipment, either directly or by way of hubs 814, as well as computing devices 860, operate as clients 863 that communicate with PPEMS 806 via interface layer 864. Computing devices 860 typically execute client software applications, such as desktop applications, mobile applications, and web applications. Computing devices 860 may represent any of computing devices 716, 718 of FIG. 7. Examples of computing devices 760 may include, but are not limited to a portable or mobile computing device (e.g., smartphone, wearable computing device, tablet), laptop computers, desktop computers, smart television platforms, and servers, to name only a few examples.

As further described in this disclosure, PPEs 862 communicate with PPEMS 806 (directly or via hubs 814) to provide streams of data acquired from embedded sensors and other monitoring circuitry and receive from PPEMS 806 alerts, configuration and other communications. Client applications executing on computing devices 860 may communicate with PPEMS 806 to send and receive information that is retrieved, stored, generated, and/or otherwise processed by services 868. For instance, the client applications may request and edit safety event information including analytical data stored at and/or managed by PPEMS 806. In some examples, client applications 861 may request and display aggregate safety event information that summarizes or otherwise aggregates numerous individual instances of safety events and corresponding data acquired from PPEs 862 and or generated by PPEMS 806. The client applications may interact with PPEMS 806 to query for analytics information about past and predicted safety events, behavior trends of workers 810, to name only a few examples. In some examples, the client applications may output for display information received from PPEMS 806 to visualize such information for users of clients 863. As further illustrated and described in below, PPEMS 806 may provide information to the client applications, which the client applications output for display in user interfaces.

Clients applications executing on computing devices 860 may be implemented for different platforms but include similar or the same functionality. For instance, a client application may be a desktop application compiled to run on a desktop operating system, such as Microsoft Windows, Apple OS X, or Linux, to name only a few examples. As another example, a client application may be a mobile application compiled to run on a mobile operating system, such as Google Android, Apple iOS, Microsoft Windows Mobile, or BlackBerry OS to name only a few examples. As another example, a client application may be a web application such as a web browser that displays web pages received from PPEMS 806. In the example of a web application, PPEMS 806 may receive requests from the web application (e.g., the web browser), process the requests, and send one or more responses back to the web application. In this way, the collection of web pages, the client-side processing web application, and the server-side processing performed by PPEMS 806 collectively provides the functionality to perform techniques of this disclosure. In this way, client applications use various services of PPEMS 806 in accordance with techniques of this disclosure, and the applications may operate within various different computing environment (e.g., embedded circuitry or processor of a PPE, a desktop operating system, mobile operating system, or web browser, to name only a few examples).

As shown in FIG. 8, PPEMS 806 includes an interface layer 864 that represents a set of application programming interfaces (API) or protocol interface presented and supported by PPEMS 806. Interface layer 864 initially receives messages from any of clients 863 for further processing at PPEMS 806. Interface layer 864 may therefore provide one or more interfaces that are available to client applications executing on clients 863. In some examples, the interfaces may be application programming interfaces (APIs) that are accessible over a network. Interface layer 864 may be implemented with one or more web servers. The one or more web servers may receive incoming requests, process and/or forward information from the requests to services 868, and provide one or more responses, based on information received from services 868, to the client application that initially sent the request. In some examples, the one or more web servers that implement interface layer 864 may include a runtime environment to deploy program logic that provides the one or more interfaces. As further described below, each service may provide a group of one or more interfaces that are accessible via interface layer 864.

In some examples, interface layer 864 may provide Representational State Transfer (RESTful) interfaces that use HTTP methods to interact with services and manipulate resources of PPEMS 806. In such examples, services 868 may generate JavaScript Object Notation (JSON) messages that interface layer 864 sends back to the client application 861 that submitted the initial request. In some examples, interface layer 864 provides web services using Simple Object Access Protocol (SOAP) to process requests from client applications 861. In still other examples, interface layer 864 may use Remote Procedure Calls (RPC) to process requests from clients 863. Upon receiving a request from a client application to use one or more services 868, interface layer 864 sends the information to application layer 866, which includes services 868.

As shown in FIG. 8, PPEMS 806 also includes an application layer 866 that represents a collection of services for implementing much of the underlying operations of PPEMS 806. Application layer 866 receives information included in requests received from client applications 861 and further processes the information according to one or more of services 868 invoked by the requests. Application layer 866 may be implemented as one or more discrete software services executing on one or more application servers, e.g., physical or virtual machines. That is, the application servers provide runtime environments for execution of services 868. In some examples, the functionality interface layer 864 as described above and the functionality of application layer 866 may be implemented at the same server.

Application layer 866 may include one or more separate software services 868, e.g., processes that communicate, e.g., via a logical service bus 870 as one example. Service bus 870 generally represents a logical interconnections or set of interfaces that allows different services to send messages to other services, such as by a publish/subscription communication model. For instance, each of services 868 may subscribe to specific types of messages based on criteria set for the respective service. When a service publishes a message of a particular type on service bus 870, other services that subscribe to messages of that type will receive the message. In this way, each of services 868 may communicate information to one another. As another example, services 868 may communicate in point-to-point fashion using sockets or other communication mechanism. Before describing the functionality of each of services 868, the layers are briefly described herein.

Data layer 872 of PPEMS 806 represents a data repository that provides persistence for information in PPEMS 806 using one or more data repositories 874. A data repository, generally, may be any data structure or software that stores and/or manages data. Examples of data repositories include but are not limited to relational databases, multi-dimensional databases, maps, and hash tables, to name only a few examples. Data layer 872 may be implemented using Relational Database Management System (RDBMS) software to manage information in data repositories 874. The RDBMS software may manage one or more data repositories 874, which may be accessed using Structured Query Language (SQL). Information in the one or more databases may be stored, retrieved, and modified using the RDBMS software. In some examples, data layer 872 may be implemented using an Object Database Management System (ODBMS), Online Analytical Processing (OLAP) database or other suitable data management system.

As shown in FIG. 8, each of services 868A-868I ("services 868") is implemented in a modular form within PPEMS 806. Although shown as separate modules for each service, in some examples the functionality of two or more services may be combined into a single module or component. Each of services 868 may be implemented in software, hardware, or a combination of hardware and software. Moreover, services 868 may be implemented as standalone devices, separate virtual machines or containers, processes, threads or software instructions generally for execution on one or more physical processors.

In some examples, one or more of services 868 may each provide one or more interfaces that are exposed through interface layer 864. Accordingly, client applications of computing devices 860 may call one or more interfaces of one or more of services 68 to perform techniques of this disclosure.

In accordance with techniques of the disclosure, services 868 may include an event processing platform including an event endpoint frontend 868A, event selector 868B, event processor 868C and high priority (HP) event processor 868D. Event endpoint frontend 868A operates as a front end interface for receiving and sending communications to PPEs 862 and hubs 814. In other words, event endpoint frontend 868A operates to as a front line interface to safety equipment deployed within environments 808 and utilized by workers 810. In some instances, event endpoint frontend 868A may be implemented as a plurality of tasks or jobs spawned to receive individual inbound communications of event streams 869 from the PPEs 862 carrying data sensed and captured by the safety equipment. When receiving event streams 869, for example, event endpoint frontend 868A may spawn tasks to quickly enqueue an inbound communication, referred to as an event, and close the communication session, thereby providing high-speed processing and scalability. Each incoming communication may, for example, carry data recently captured data representing sensed conditions, motions, temperatures, actions or other data, generally referred to as events. Communications exchanged between the event endpoint frontend 868A and the PPEs may be real-time or pseudo real-time depending on communication delays and continuity.

Event selector 868B operates on the stream of events 869 received from PPEs 862 and/or hubs 814 via frontend 868A and determines, based on rules or classifications, priorities associated with the incoming events. Based on the priorities, event selector 868B enqueues the events for subsequent processing by event processor 868C or high priority (HP) event processor 868D. Additional computational resources and objects may be dedicated to HP event processor 868D so as to ensure responsiveness to critical events, such as incorrect usage of PPEs, use of incorrect filters and/or respirators based on geographic locations and conditions, failure to properly secure SRLs 811 and the like. Responsive to processing high priority events, HP event processor 868D may immediately invoke notification service 68E to generate alerts, instructions, warnings or other similar messages to be output to SRLs 811, respirators 813, hubs 814 and/or remote users 820, 824. Events not classified as high priority are consumed and processed by event processor 868C.

In general, event processor 868C or high priority (HP) event processor 68D operate on the incoming streams of events to update event data 874A within data repositories 874. In general, event data 874A may include all or a subset of usage data obtained from PPEs 862. For example, in some instances, event data 874A may include entire streams of samples of data obtained from electronic sensors of PPEs 862. In other instances, event data 874A may include a subset of such data, e.g., associated with a particular time period or activity of PPEs 862.

Event processors 868C, 868D may create, read, update, and delete event information stored in event data 874A. Event information for may be stored in a respective database record as a structure that includes name/value pairs of information, such as data tables specified in row/column format. For instance, a name (e.g., column) may be "worker ID" and a value may be an employee identification number. An event record may include information such as, but not limited to: worker identification, PPE identification, acquisition timestamp(s) and data indicative of one or more sensed parameters.

In addition, event selector 868B directs the incoming stream of events to stream analytics service 868F, which is configured to perform in depth processing of the incoming stream of events to perform real-time analytics. Stream analytics service 868F may, for example, be configured to process and compare multiple streams of event data 874A with historical data and models 874B in real-time as event data 874A is received. In this way, stream analytic service 868D may be configured to detect anomalies, transform incoming event data values, trigger alerts upon detecting safety concerns based on conditions or worker behaviors. Historical data and models 874B may include, for example, specified safety rules, business rules and the like. In addition, stream analytic service 868D may generate output for communicating to PPPEs 862 by notification service 868F or computing devices 860 by way of record management and reporting service 868D.

In this way, analytics service 868F processes inbound streams of events, potentially hundreds or thousands of streams of events, from enabled safety PPEs 862 utilized by workers 810 within environments 808 to apply historical data and models 874B to compute assertions, such as identified anomalies or predicted occurrences of imminent safety events based on conditions or behavior patterns of the workers. Analytics service 868D may publish the assertions to notification service 868F and/or record management by service bus 870 for output to any of clients 863.

In this way, analytics service 868F may be configured as an active safety management system that predicts imminent safety concerns and provides real-time alerting and reporting. In addition, analytics service 868F may be a decision support system that provides techniques for processing inbound streams of event data to generate assertions in the form of statistics, conclusions, and/or recommendations on an aggregate or individualized worker and/or PPE basis for enterprises, safety officers and other remote users. For instance, analytics service 868F may apply historical data and models 874B to determine, for a particular worker, the likelihood that a safety event is imminent for the worker based on detected behavior or activity patterns, environmental conditions and geographic locations. In some examples, analytics service 868F may determine whether a worker is currently impaired, e.g., due to exhaustion, sickness or alcohol/drug use, and may require intervention to prevent safety events. As yet another example, analytics service 68F may provide comparative ratings of workers or type of safety equipment in a particular environment 808.

Hence, analytics service 868F may maintain or otherwise use one or more models that provide risk metrics to predict safety events. Analytics service 868F may also generate order sets, recommendations, and quality measures. In some examples, analytics service 868F may generate user interfaces based on processing information stored by PPEMS 806 to provide actionable information to any of clients 863. For example, analytics service 868F may generate dashboards, alert notifications, reports and the like for output at any of clients 863. Such information may provide various insights regarding baseline ("normal") operation across worker populations, identifications of any anomalous workers engaging in abnormal activities that may potentially expose the worker to risks, identifications of any geographic regions within environments for which unusually anomalous (e.g., high) safety events have been or are predicted to occur, identifications of any of environments exhibiting anomalous occurrences of safety events relative to other environments, and the like.

Although other technologies can be used, in one example implementation, analytics service 868F utilizes machine learning when operating on streams of safety events so as to perform real-time analytics. That is, analytics service 868F includes executable code generated by application of machine learning to training data of event streams and known safety events to detect patterns. The executable code may take the form of software instructions or rule sets and is generally referred to as a model that can subsequently be applied to event streams 869 for detecting similar patterns and predicting upcoming events.

Analytics service 868F may, in some example, generate separate models for a particular worker, a particular population of workers, a particular environment, or combinations thereof. Analytics service 868F may update the models based on usage data received from PPEs 862. For example, analytics service 868F may update the models for a particular worker, a particular population of workers, a particular environment, or combinations thereof based on data received from PPEs 862. In some examples, usage data may include incident reports, air monitoring systems, manufacturing production systems, or any other information that may be used to a train a model.

Alternatively, or in addition, analytics service 868F may communicate all or portions of the generated code and/or the machine learning models to hubs 816 (or PPEs 862) for execution thereon so as to provide local alerting in near-real time to PPEs. Example machine learning techniques that may be employed to generate models 874B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

Record management and reporting service 868G processes and responds to messages and queries received from computing devices 860 via interface layer 864. For example, record management and reporting service 868G may receive requests from client computing devices for event data related to individual workers, populations or sample sets of workers, geographic regions of environments 808 or environments 808 as a whole, individual or groups/types of PPEs 862. In response, record management and reporting service 868G accesses event information based on the request. Upon retrieving the event data, record management and reporting service 868G constructs an output response to the client application that initially requested the information. In some examples, the data may be included in a document, such as an HTML document, or the data may be encoded in a JSON format or presented by a dashboard application executing on the requesting client computing device. For instance, as further described in this disclosure, example user interfaces that include the event information are depicted in the figures.

As additional examples, record management and reporting service 868G may receive requests to find, analyze, and correlate PPE event information. For instance, record management and reporting service 868G may receive a query request from a client application for event data 874A over a historical time frame, such as a user can view PPE event information over a period of time and/or a computing device can analyze the PPE event information over the period of time.

In example implementations, services 868 may also include security service 868H that authenticate and authorize users and requests with PPEMS 806. Specifically, security service 868H may receive authentication requests from client applications and/or other services 868 to access data in data layer 872 and/or perform processing in application layer 866. An authentication request may include credentials, such as a username and password. Security service 868H may query security data 874A to determine whether the username and password combination is valid. Configuration data 874D may include security data in the form of authorization credentials, policies, and any other information for controlling access to PPEMS 806. As described above, security data 874A may include authorization credentials, such as combinations of valid usernames and passwords for authorized users of PPEMS 806. Other credentials may include device identifiers or device profiles that are allowed to access PPEMS 806.

Security service 868H may provide audit and logging functionality for operations performed at PPEMS 806. For instance, security service 868H may log operations performed by services 868 and/or data accessed by services 868 in data layer 872. Security service 868H may store audit information such as logged operations, accessed data, and rule processing results in audit data 874C. In some examples, security service 868H may generate events in response to one or more rules being satisfied. Security service 868H may store data indicating the events in audit data 874C.

In the example of FIG. 8, a safety manager may initially configure one or more safety rules. As such, remote user 824 may provide one or more user inputs at computing device 818 that configure a set of safety rules for work environment 808A and 808B. For instance, a computing device 860 of the safety manager may send a message that defines or specifies the safety rules. Such message may include data to select or create conditions and actions of the safety rules. PPEMS 806 may receive the message at interface layer 864 which forwards the message to rule configuration component 8681. Rule configuration component 8681 may be combination of hardware and/or software that provides for rule configuration including, but not limited to: providing a user interface to specify conditions and actions of rules, receive, organize, store, and update rules included in safety rules data store 874E.

Safety rules data store 875E may be a data store that includes data representing one or more safety rules. Safety rules data store 874E may be any suitable data store such as a relational database system, online analytical processing database, object-oriented database, or any other type of data store. When rule configuration component 681 receives data defining safety rules from computing device 860 of the safety manager, rule configuration component 8681 may store the safety rules in safety rules data store 875E.

In some examples, storing the safety rules may include associating a safety rule with context data, such that rule configuration component 8681 may perform a lookup to select safety rules associated with matching context data. Context data may include any data describing or characterizing the properties or operation of a worker, worker environment, article of PPE, or any other entity. Context data of a worker may include, but is not limited to: a unique identifier of a worker, type of worker, role of worker, physiological or biometric properties of a worker, experience of a worker, training of a worker, time worked by a worker over a particular time interval, location of the worker, or any other data that describes or characterizes a worker. Context data of an article of PPE may include, but is not limited to: a unique identifier of the article of PPE; a type of PPE of the article of PPE; a usage time of the article of PPE over a particular time interval; a lifetime of the PPE; a component included within the article of PPE; a usage history across multiple users of the article of PPE; contaminants, hazards, or other physical conditions detected by the PPE, expiration date of the article of PPE; operating metrics of the article of PPE. Context data for a work environment may include, but is not limited to: a location of a work environment, a boundary or perimeter of a work environment, an area of a work environment, hazards within a work environment, physical conditions of a work environment, permits for a work environment, equipment within a work environment, owner of a work environment, responsible supervisor and/or safety manager for a work environment.

Table 1, shown below, includes a non-limiting set of rules that may be stored to safety rules data store 874E:

TABLE 1

SAFETY RULES

Hub shall immediately assert an "Attention Initial" Alert if Visor Position Status is OPEN in current location requiring Visor Open Allow = NO
Hub shall immediately assert a "Critical Initial" Alert if Filter Type Status is not equal to Filter Type or no filter found required by current location
Hub shall store all alerts in a queue.
Critical Alerts shall be highest priority in alert queue
Attention Alerts shall have secondary priority in alert queue
Hub shall immediately remove an alert from the queue if its conditions causing the alert have been corrected
A newly added alert to the alert queue shall be flagged as "Active", if it is higher priority than any other alarms in the queue.
A newly added alert to the alert queue shall be flagged as "Active", if all other alarms in the queue are Acknowledged or Notify
A newly added alert to the alert queue shall be flagged as "Pending" if an Active alert already exists in the queue and the newly added alert is lower in priority than the currently Active alert
If an Active alert in the queue is replaced by a new Active alert because of priority, the replaced alert shall be flagged as "Pending"
An active alert shall enable its respective haptic feedback and LED pattern
Hub shall assert an Acknowledge event when user presses and releases button within <3 seconds. (Button_Tap)
Upon an Acknowledge event the Hub shall immediately flag the currently Active alert as Acknowledged, if any Active alerts are in the queue.
An Acknowledged alert shall disable its respective haptic feedback and LED pattern
Upon an Acknowledge event the Hub shall immediately flag the highest priority Pending alert as Active, if any Pending alerts exist in the queue.
Upon an Acknowledge event the Hub shall immediately flag the highest priority Acknowledged alert as Notify, if no Active alerts or Pending exist in the queue.
A Notify alert shall disable its respective haptic feedback and enable its LED pattern
Immediate Cloud Updates - Hub shall send safety violation asserted message via Wi-Fi to cloud service immediately upon assertion of alert
Immediate Worker Interface Updates - Hub shall send safety rule violation alerts asserted message via BLE to Worker Interface immediately upon assertion of alert
Immediate Cloud Updates - Hub shall send safety violation deasserted message via Wi-Fi to cloud service immediately upon deassertion of alert
Immediate Worker Interface Updates - Hub shall send safety violation deasserted message via BLE to Worker Interface immediately upon deassertion of alert It should be understood that the examples of Table 1 are provided for purposes of illustration only, and that other rules may be developed.

According to aspects of this disclosure, the rules may be used for purposes of reporting, to generate alerts, or the like. In an example for purposes of illustration, worker 810A may be equipped with respirator 813A and data hub 814A. Respirator 813A may include a filter to remove particulates but not organic vapors. Data hub 814A may be initially configured with and store a unique identifier of worker 810A. When initially assigning the respirator 813A and data hub to worker 810A, a computing device operated by worker 810A and/or a safety manager may cause RMRS 868G to store a mapping in work relation data 874F. Work relation data 874F may include mappings between data that corresponds to PPE, workers, and work environments. Work relation data 874F may be any suitable datastore for storing, retrieving, updating and deleting data. RMRS 868G may store a mapping between the unique identifier of worker 810A and a unique device identifier of data hub 814A. Work relation data store 874F may also map a worker to an environment.

According to aspects of this disclosure, as noted above, PPEMS 806 may additionally or alternatively apply analytics to predict the likelihood of a safety event. As noted above, a safety event may refer to activities of a worker 810 using PPE 862, a condition of PPE 862, or a hazardous environmental condition (e.g., that the likelihood of a safety event is relatively high, that the environment is dangerous, that SRL 811 is malfunctioning, that one or more components of SRL 811 need to be repaired or replaced, or the like). For example, PPEMS 806 may determine the likelihood of a safety event based on application of usage data from PPE 862 to historical data and models 874B. That is, PEMS 806 may apply historical data and models 874B to usage data from respirators 813 in order to compute assertions, such as anomalies or predicted occurrences of imminent safety events based on environmental conditions or behavior patterns of a worker using a respirator 813.

PPEMS 806 may apply analytics to identify relationships or correlations between sensed data from respirators 813, environmental conditions of environment in which respirators 813 are located, a geographic region in which respirators 813 are located, and/or other factors. PPEMS 806 may determine, based on the data acquired across populations of workers 810, which particular activities, possibly within certain environment or geographic region, lead to, or are predicted to lead to, unusually high occurrences of safety events. PPEMS 806 may generate alert data based on the analysis of the usage data and transmit the alert data to PPEs 862 and/or hubs 814. Hence, according to aspects of this disclosure, PPEMS 806 may determine usage data of respirator 813, generate status indications, determine performance analytics, and/or perform prospective/preemptive actions based on a likelihood of a safety event.

For example, according to aspects of this disclosure, usage data from respirators 813 may be used to determine usage statistics. For example, PPEMS 806 may determine, based on usage data from respirators 813, a length of time that one or more components of respirator 813 (e.g., head top, blower, and/or filter) have been in use, an instantaneous velocity or acceleration of worker 810 (e.g., based on an accelerometer included in respirators 813 or hubs 814), a temperature of one or more components of respirator 813 and/or worker 810, a location of worker 810, a number of times or frequency with which a worker 810 has performed a self-check of respirator 813 or other PPE, a number of times or frequency with which a visor of respirator 813 has been opened or closed, a filter/cartridge consumption rate, fan/blower usage (e.g., time in use, speed, or the like), battery usage (e.g., charge cycles), or the like.

According to aspects of this disclosure, PPEMS 806 may use the usage data to characterize activity of worker 810. For example, PPEMS 806 may establish patterns of productive and nonproductive time (e.g., based on operation of respirator 813 and/or movement of worker 810), categorize worker movements, identify key motions, and/or infer occurrence of key events. That is, PPEMS 806 may obtain the usage data, analyze the usage data using services 868 (e.g., by comparing the usage data to data from known activities/events), and generate an output based on the analysis.

In some examples, the usage statistics may be used to determine when respirator 813 is in need of maintenance or replacement. For example, PPEMS 806 may compare the usage data to data indicative of normally operating respirators 813 in order to identify defects or anomalies. In other examples, PPEMS 806 may also compare the usage data to data indicative of a known service life statistics of respirators 813. The usage statistics may also be used to provide an understanding how respirators 813 are used by workers 810 to product developers in order to improve product designs and performance. In still other examples, the usage statistics may be used to gathering human performance metadata to develop product specifications. In still other examples, the usage statistics may be used as a competitive benchmarking tool. For example, usage data may be compared between customers of respirators 813 to evaluate metrics (e.g. productivity, compliance, or the like) between entire populations of workers outfitted with respirators 813.

Additionally or alternatively, according to aspects of this disclosure, usage data from respirators 813 may be used to determine status indications. For example, PPEMS 806 may determine that a visor of a respirator 813 is up in hazardous work area. PPEMS 806 may also determine that a worker 810 is fitted with improper equipment (e.g., an improper filter for a specified area), or that a worker 810 is present in a restricted/closed area. PPEMS 806 may also determine whether worker temperature exceeds a threshold, e.g., in order to prevent heat stress. PPEMS 806 may also determine when a worker 810 has experienced an impact, such as a fall.

Additionally or alternatively, according to aspects of this disclosure, usage data from respirators 813 may be used to assess performance of worker 810 wearing respirator 813. For example, PPEMS 806 may, based on usage data from respirators 813, recognize motion that may indicate a pending fall by worker 810 (e.g., via one or more accelerometers included in respirators 813 and/or hubs 814). In some instances, PPEMS 6 may, based on usage data from respirators 813, infer that a fall has occurred or that worker 810 is incapacitated. PPEMS 806 may also perform fall data analysis after a fall has occurred and/or determine temperature, humidity and other environmental conditions as they relate to the likelihood of safety events.

As another example, PPEMS 806 may, based on usage data from respirators 813, recognize motion that may indicate fatigue or impairment of worker 810. For example, PPEMS 806 may apply usage data from respirators 813 to a safety learning model that characterizes a motion of a user of at least one respirator. In this example, PPEMS 806 may determine that the motion of a worker 810 over a time period is anomalous for the worker 810 or a population of workers 810 using respirators 813.

Additionally or alternatively, according to aspects of this disclosure, usage data from respirators 813 may be used to determine alerts and/or actively control operation of respirators 813. For example, PPEMS 806 may determine that a safety event such as equipment failure, a fall, or the like is imminent. PPEMS 6 may send data to respirators 813 to change an operating condition of respirators 813. In an example for purposes of illustration, PPEMS 806 may apply usage data to a safety learning model that characterizes an expenditure of a filter of one of respirators 813. In this example, PPEMS 806 may determine that the expenditure is higher than an expected expenditure for an environment, e.g., based on conditions sensed in the environment, usage data gathered from other workers 810 in the environment, or the like. PPEMS 806 may generate and transmit an alert to worker 810 that indicates that worker 810 should leave the environment and/or active control of respirator 813. For example, PPEMS 806 may cause respirator to reduce a blower speed of a blower of respirator 813 in order to provide worker 810 with substantial time to exit the environment.

PPEMS 806 may generate, in some examples, a warning when worker 810 is near a hazard (e.g., based on location data gathered from a location sensor (GPS or the like) of respirators 813). PPEMS 806 may also applying usage data to a safety learning model that characterizes a temperature of worker 810. In this example, PPEMS 806 may determine that the temperature exceeds a temperature associated with safe activity over the time period and alert worker 810 to the potential for a safety event due to the temperature.

In another example, PPEMS 806 may schedule preventative maintenance or automatically purchase components for respirators 813 based on usage data. For example, PPEMS 806 may determine a number of hours a blower of a respirator 813 has been in operation, and schedule preventative maintenance of the blower based on such data. PPEMS 806 may automatically order a filter for respirator 813 based on historical and/or current usage data from the filter.

Again, PPEMS 806 may determine the above-described performance characteristics and/or generate the alert data based on application of the usage data to one or more safety learning models that characterizes activity of a user of one of respirators 813. The safety learning models may be trained based on historical data or known safety events. However, while the determinations are described with respect to PPEMS 806, as described in greater detail herein, one or more other computing devices, such as hubs 814 or respirators 813 may be configured to perform all or a subset of such functionality.

In some examples, a safety learning model is trained using supervised and/or reinforcement learning techniques. The safety learning model may be implemented using any number of models for supervised and/or reinforcement learning, such as but not limited to, an artificial neural networks, a decision tree, naïve Bayes network, support vector machine, or k-nearest neighbor model, to name only a few examples. In some examples, PPEMS 806 initially trains the safety learning model based on a training set of metrics and corresponding to safety events. The training set may include a set of feature vectors, where each feature in the feature vector represents a value for a particular metric. As further example description, PPEMS 806 may select a training set comprising a set of training instances, each training instance comprising an association between usage data and a safety event. The usage data may comprise one or more metrics that characterize at least one of a user, a work environment, or one or more articles of PPE. PPEMS 806 may, for each training instance in the training set, modify, based on particular usage data and a particular safety event of the training instance, the safety learning model to change a likelihood predicted by the safety learning model for the particular safety event in response to subsequent usage data applied to the safety learning model. In some examples, the training instances may be based on real-time or periodic data generated while PPEMS 806 managing data for one or more articles of PPE, workers, and/or work environments. As such, one or more training instances of the set of training instances may be generated from use of one or more articles of PPE after PPEMS 806 performs operations relating to the detection or prediction of a safety event for PPE, workers, and/or work environments that are currently in use, active, or in operation.

Some example metrics may include any characteristics or data described in this disclosure that relate to PPE, a worker, or a work environment, to name only a few examples. For instance, example metrics may include but are not limited to: worker identity, worker motion, worker location, worker age, worker experience, worker physiological parameters (e.g., heart rate, temperature, blood oxygen level, chemical compositions in blood, or any other measurable physiological parameter), or any other data descriptive of a worker or worker behavior. Example metrics may include but are not limited to: PPE type, PPE usage, PPE age, PPE operations, or any other data descriptive of PPE or PPE use. Example metrics may include but are not limited to: work environment type, work environment location, work environment temperature, work environment hazards, work environment size, or any other data descriptive of a work environment.

Each feature vector may also have a corresponding safety event. As described in this disclosure, a safety event may include but is not limited to: activities of a user of personal protective equipment (PPE), a condition of the PPE, or a hazardous environmental condition to name only a few examples. By training a safety learning model based on the training set, a safety learning model may be configured by PPEMS 806 to, when applying a particular feature vector to the safety learning model, generate higher probabilities or scores for safety events that correspond to training feature vectors that are more similar to the particular feature set. In the same way, the safety learning model may be configured by PPEMS 806 to, when applying a particular feature vector to the safety learning model, generate lower probabilities or scores for safety events that correspond to training feature vectors that are less similar to the particular feature set. Accordingly, the safety learning model may be trained, such that upon receiving a feature vector of metrics, the safety learning model may output one or more probabilities or scores that indicate likelihoods of safety events based on the feature vector. As such, PPEMS 806 may select likelihood of the occurrence as a highest likelihood of occurrence of a safety event in the set of likelihoods of safety events.

In some instances, PPEMS 806 may apply analytics for combinations of PPE. For example, PPEMS 806 may draw correlations between users of respirators 813 and/or the other PPE (such as fall protection equipment, head protection equipment, hearing protection equipment, or the like) that is used with respirators 813. That is, in some instances, PPEMS 806 may determine the likelihood of a safety event based not only on usage data from respirators 813, but also from usage data from other PPE being used with respirators 813. In such instances, PPEMS 806 may include one or more safety learning models that are constructed from data of known safety events from one or more devices other than respirators 813 that are in use with respirators 813.

In some examples, a safety learning model is based on safety events from one or more of a worker, article of PPE, and/or work environment having similar characteristics (e.g., of a same type). In some examples the "same type" may refer to identical but separate instances of PPE. In other examples the "same type" may not refer to identical instances of PPE. For instance, although not identical, a same type may refer to PPE in a same class or category of PPE, same model of PPE, or same set of one or more shared functional or physical characteristics, to name only a few examples. Similarly, a same type of work environment or worker may refer to identical but separate instances of work environment types or worker types. In other examples, although not identical, a same type may refer to a worker or work environment in a same class or category of worker or work environment or same set of one or more shared behavioral, physiological, environmental characteristics, to name only a few examples.

In some examples, to apply the usage data to a model, PPEMS 806 may generate a structure, such as a feature vector, in which the usage data is stored. The feature vector may include a set of values that correspond to metrics (e.g., characterizing PPE, worker, work environment, to name a few examples), where the set of values are included in the usage data. The model may receive the feature vector as input, and based on one or more relations defined by the model (e.g., probabilistic, deterministic or other functions within the knowledge of one of ordinary skill in the art) that has been trained, the model may output one or more probabilities or scores that indicate likelihoods of safety events based on the feature vector.

In general, while certain techniques or functions are described herein as being performed by certain components, e.g., PPEMS 806, respirators 813, or hubs 814, it should be understood that the techniques of this disclosure are not limited in this way. That is, certain techniques described herein may be performed by one or more of the components of the described systems. For example, in some instances, respirators 813 may have a relatively limited sensor set and/or processing power. In such instances, one of hubs 814 and/or PPEMS 806 may be responsible for most or all of the processing of usage data, determining the likelihood of a safety event, and the like. In other examples, respirators 813 and/or hubs 814 may have additional sensors, additional processing power, and/or additional memory, allowing for respirators 813 and/or hubs 814 to perform additional techniques. Determinations regarding which components are responsible for performing techniques may be based, for example, on processing costs, financial costs, power consumption, or the like.

In some examples in accordance with this disclosure, a system may include various components configured to allow safety professionals to manage area inspections, worker inspections, worker health and safety compliance training. For example, a system may include one or more computing devices configured to process and analyze data generated by one or more sensors embedded within an article of personal protective equipment.

In the example depicted in FIG. 8, PPEMS 806 may include processing circuitry, such as processing circuitry 580 depicted in FIG. 5B, configured to receive data indicative of an individual's physiological condition. In FIG. 8, worker 810 is depicted wearing an article of personal protective equipment (PPE) 813. Although FIG. 8 depicts PPE 813 as respiratory protection, PPE 813 could also include hearing protection, for example earmuffs 10 as shown in FIG. 1. PPE 813 may include one more embedded sensors, such as physiological sensor 650 depicted in FIGS. 5A, 5B, and 6, configured to receive signals from the body of worker 810. In some examples, PPE 813 may include a photoplethysmograph sensor or other optical sensor configured to determine the blood oximetry or other biomarkers of worker 810. In other examples, PPE 813 may include an EEG and/or EDA sensor and one or more electrodes configured to monitor the brain activity and/or electrodermal activity of worker 810.

In some examples, PPE 813 may include processing circuitry configured to analyze data from a physiological sensor. In other examples, PPE 813 may include transmission means, such as data communication hubs 814, configured to transmit data from the physiological sensor into processing circuitry within PPEMS 806, to determine a probability of a significant physiological condition.

For example, rule configuration component 8681 within PPEMS 806 may store one or more rules indicating threshold safety measurements corresponding to predetermined probabilities of concerning physiological conditions. Components 868A-868D, in particular processor 868C may retrieve one or more threshold safety measurements from rule configuration component 8681, and compare the rules to one or more current sensor measurements to determine a likelihood of 810 having a concerning physiological condition.

Upon determination of a significant probability of a physiological condition, such as determining a threshold data measurement, notification service 868E within PPEMS 806 may be configured to generate and output an alert. The alert may be sent to worker 810, such as via audio, visual, or haptic feedback. In other examples, the alert may be sent to safety station 815 or mobile device 860. Mobile device 860, such as a pager, mobile phone, or personal computing device, may be held by worker 810, or by a remote user, such as a workplace safety supervisor, so that he may activate additional safety protocols to protect the health of worker 810.

Figure 9:
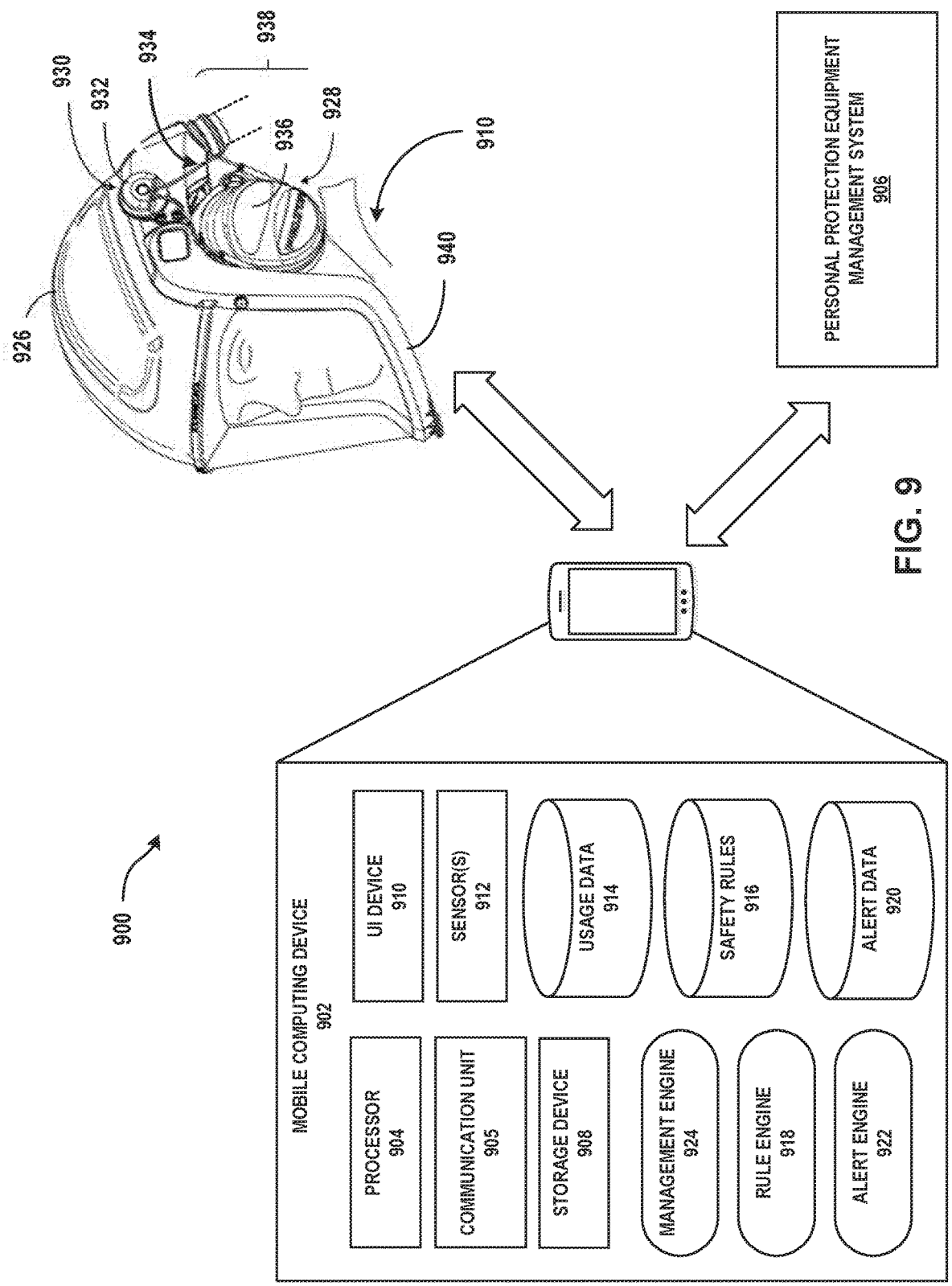
FIG. 9 illustrates an example system including a mobile computing device, a set of personal protection equipment communicatively coupled to the mobile computing device, and a personal protection equipment management system communicatively coupled to the mobile computing device, in accordance with techniques of this disclosure.

FIG. 9 illustrates an example system including a mobile computing device, a set of personal protection equipment communicatively coupled to the mobile computing device, and a personal protection equipment management system communicatively coupled to the mobile computing device, in accordance with techniques of this disclosure. For purposes of illustration only, system 900 includes mobile computing device 902, which may be an example of hub 714A in FIG. 7.

FIG. 9 illustrates components of mobile computing device 902 including processor 904, communication unit 905, storage device 908, user-interface (UI) device 910, sensors 912, usage data 914, safety rules 916, rule engine 918, alert data 920, alert engine 922, and management engine 924. As noted above, mobile computing device 902 represents one example of hubs 714 shown in FIG. 7. Many other examples of mobile computing device 902 may be used in other instances and may include a subset of the components included in example mobile computing device 902 or may include additional components not shown example mobile computing device 902 in FIG. 9.

In some examples, mobile computing device 902 may be an intrinsically safe computing device, smartphone, wrist- or head-wearable computing device, or any other computing device that may include a set, subset, or superset of functionality or components as shown in mobile computing device 902. Communication channels may interconnect each of the components in mobile computing device 902 for inter-component communications (physically, communicatively, and/or operatively). In some examples, communication channels may include a hardware bus, a network connection, one or more inter-process communication data structures, or any other components for communicating data between hardware and/or software.

Mobile computing device 902 may also include a power source, such as a battery, to provide power to components shown in mobile computing device 902. A rechargeable battery, such as a Lithium Ion battery, can provide a compact and long-life source of power. Mobile computing device 902 may be adapted to have electrical contacts exposed or accessible from the exterior of the hub to allow recharging the mobile computing device 902. As noted above, mobile computing device 902 may be portable such that it can be carried or worn by a user. Mobile computing device 902 can also be personal, such that it is used by an individual and communicates with personal protective equipment (PPE) assigned to that individual. In FIG. 9, mobile computing device 902 may be secured to a user by a strap. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

One or more processors 904 may implement functionality and/or execute instructions within mobile computing device 902. For example, processor 904 may receive and execute instructions stored by storage device 908. These instructions executed by processor 904 may cause mobile computing device 902 to store and/or modify information, within storage devices 908 during program execution. Processors 904 may execute instructions of components, such as rule engine 918 and alert engine 922 to perform one or more operations in accordance with techniques of this disclosure. That is, rule engine 918 and alert engine 922 may be operable by processor 904 to perform various functions described herein.

One or more communication units 905 of mobile computing device 902 may communicate with external devices by transmitting and/or receiving data. For example, mobile computing device 902 may use communication units 905 to transmit and/or receive radio signals on a radio network such as a cellular radio network. In some examples, communication units 905 may transmit and/or receive satellite signals on a satellite network such as a Global Positioning System (GPS) network. Examples of communication units 905 include a network interface card (e.g. such as an Ethernet card), an optical transceiver, a radio frequency transceiver, a GPS receiver, or any other type of device that can send and/or receive information. Other examples of communication units 905 may include Bluetooth®, GPS, 3G, 4G, and Wi-Fi® radios found in mobile devices as well as Universal Serial Bus (USB) controllers and the like.

One or more storage devices 908 within mobile computing device 902 may store information for processing during operation of mobile computing device 902. In some examples, storage device 908 is a temporary memory, meaning that a primary purpose of storage device 908 is not long-term storage. Storage device 908 may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage device 908 may, in some examples, also include one or more computer-readable storage media. Storage device 908 may be configured to store larger amounts of information than volatile memory. Storage device 908 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage device 308 may store program instructions and/or data associated with components such as rule engine 918 and alert engine 922.

UI device 910 may be configured to receive user input and/or output information to a user. One or more input components of UI device 910 may receive input. Examples of input are tactile, audio, kinetic, and optical input, to name only a few examples. UI device 910 of mobile computing device 902, in one example, include a mouse, keyboard, voice responsive system, video camera, buttons, control pad, microphone or any other type of device for detecting input from a human or machine. In some examples, UI device 910 may be a presence-sensitive input component, which may include a presence-sensitive screen, touch-sensitive screen, etc.

One or more output components of UI device 910 may generate output. Examples of output are data, tactile, audio, and video output. Output components of UI device 910, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components may be integrated with mobile computing device 902 in some examples.

UI device 910 may include a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

Sensors 912 may include one or more sensors that generate data indicative of an activity of a worker 910 associated with mobile computing device 902 and/or data indicative of an environment in which mobile computing device 902 is located. Sensors 912 may include, as examples, physiological sensors, such as EEG sensors or PPG sensors, one or more accelerometers, one or more sensors to detect conditions present in a particular environment (e.g., sensors for measuring temperature, humidity, particulate content, noise levels, air quality, or any variety of other characteristics of environments in which respirator 913 may be used), or a variety of other sensors.

Mobile computing device 902 may store usage data 914 from components of system 900. For example, as described herein, components of system 900 (or any other examples of respirators 913) may generate data regarding operation of system 900 that is indicative of activities of worker 910 and transmit the data in real-time or near real-time to mobile computing device 902.

In some examples, mobile computing device 902 may immediately relay usage data 914 to another computing device, such as PPEMS 906, via communication unit 905. In other examples, storage device 908 may store usage data 914 for some time prior to uploading the data to another device. For example, in some instances, communication unit 905 may be able to communicate with system 900 but may not have network connectivity, e.g., due to an environment in which system 900 is located and/or network outages. In such instances, mobile computing device 902 may store usage data 914 to storage device 908, which may allow the usage data to be uploaded to another device upon a network connection becoming available. Mobile computing device 902 may store safety rules 916 as described in this disclosure. Safety rules 916 may be stored in any suitable data store as described in this disclosure.

System 900 may include head top 926 and hearing protector 928, in accordance with this disclosure. As shown in FIG. 9, head top 926 may include structure and functionality that is similar to or the same as respirator 713A as described in FIG. 7 and other embodiments of this disclosures. Head top 926 (or other head-worn device, such as a head band) may include hearing protector 928 that includes, ear muff attachment assembly 930. Ear muff attachment assembly 930 may include housing 932, an arm set 934, and ear muffs 936. Hearing protector 928 may include two separate ear muff cups 936, one of which is visible in FIG. 9 and the other on the opposite side of the user's head and similarly configured to the visible ear muff cup in FIG. 9. Arm set 934 is rotatable between one or more different positions, such that hearing protector 928 may be adjusted and/or toggled, for example, between "active" and "standby" positions (or one or more additional intermediate positions). In an active position, hearing protector 928 is configured to at least partially cover a user's ear. In a standby mode, hearing protector 928 is in a raised position away from and/or out of contact with a user's head. A user is able to switch between active and standby positions when entering or leaving an area necessitating hearing protection, for example, or as may be desired by the user. Adjustment to a standby position allows hearing protector 928 to be readily available for the user to move hearing protector 928 into an active position in which hearing protection is provided without the need to carry or store ear muffs.

Ear muff attachment assembly 930 may be attached directly or indirectly to a helmet, hard hat, strap, head band, or other head support, such as a head top 26. Head top 926 may be worn simultaneously with, and provide a support for, ear muff attachment assembly 930. Ear muff attachment assembly 930 is attached to an outer surface of head top 926, and arm set 934 extends generally downwardly around an edge of head top 926 such that ear muffs of hearing protector 928 may be desirably positioned to cover a user's ear.

In various examples, head top 926 and ear muff attachment assembly 930 may be joined using various suitable attachment components, such as snap-fit components, rivets, mechanical fasteners, adhesive, or other suitable attachment components as known in the art. Ear muffs of hearing protector 928 are configured to cover at least a portion of a user's ear and/or head. In FIG. 9, ear muffs exhibit a cup shape and include a cushion and a sound absorber (not shown). Cushions are configured to contact a user's head and/or ear when ear muffs are in an active position forming an appropriate seal to prevent sound waves from entering. Arm set 934 extends outwardly from head top 926 and is configured to carry ear muffs of hearing protector 928.

In the example of FIG. 9, ear muff attachment assembly 930 may have positional or motion sensors to detect whether the ear muffs are in the standby or active position. The positional or motion sensor may generate one or more signals that indicate a particular position from a set of one or more positions. The signals may indicate one or more position values (e.g., discrete "active"/"standby" values, numeric position representations, or any other suitable encoding or measurement values). If, for example, the standby condition is detected by the one or more positional or motion sensors and if an environmental sound detector detects unsafe sound levels, then a computing device may generate an indication of output, such as a notification, log entry, or other type of output. In some examples, the indication of output may be audible, visual, haptic, or any other physical sensory output.

In high noise environment workers may be required to use hearing protection in the form of ear plugs or ear muffs. Ear muffs typically comprise cup shaped shell with a sound absorbing liner that seals against the ear of the user. Many workers also use head and/or face protection while wearing ear muffs. Therefore, many ear muff models are designed to attach to a helmet, hard hat or other headgear, such as shown in FIG. 9. The ear muffs may be affixed to the headgear via an arm that attaches to the headgear and is adjustable between various positions over or away from the worker's ear.

As described above, headgear mounted ear muffs rotate between two positions: the active position where the ear muffs cover the worker's ears providing hearing protection, and the standby position where the ear muffs are rotated up and away from the ears. While in the standby position the ear muff does not provide hearing protection to the worker. In some types of headgear attached ear muffs, the muffs can be pivoted outward away from the ear of the user in the standby position. In this case, the ear muffs rest at a small distance away from the head of the user. In the active position, the muffs are pivoted toward the head where it is sealed around the ears of the user providing hearing protection.

Returning to mobile computing device 902, safety rules 916 may include threshold information both for a length of time visor 940 is allowed to be in an open position before an alert is generated, and the level or type of contaminants that will trigger an alert. For example, when mobile computing device 902 receives information from an environmental beacon that there are no hazards present in the environment, the threshold for the visor 940 being in the open position may be infinite. If a hazard is present in the environment, then the threshold may be determined based upon the concern of the threat to the user. Radiation, dangerous gases, or toxic fumes would all require assignment of the threshold to be on the order of one second or less.

Thresholds for head top temperature can be used to predict, e.g., by PPEMS 906, heat related illness and more frequent hydration and/or rest periods can be recommended to the user. Thresholds can be used for predicted battery run time. As the battery nears selectable remaining run time, the user can be notified/warned to complete their current task and seek a fresh battery. When a threshold is exceeded for a specific environmental hazard, an urgent alert can be given to the user to evacuate the immediate area. Thresholds can be customized to various levels of openness for the visor. In other words, a threshold for the amount of a time the visor may be open without triggering an alarm may be longer if the visor is in the partially open position as compared to the open position.

Reaching different thresholds set forth in safety rules 916 may result in triggering different types of alerts or alarms. For example, alarms may be informational (not requiring a user response), urgent (repeated and requiring a response or acknowledgement from a user), or emergency (requiring immediate action from a user.) The type of alert or alarm can be tailored to the environment. Different types of alerts and alarms can be coupled together to get user attention. In some instances, a user may be able to "snooze" an alert or alarm.

Rule engine 918 may be a combination of hardware and software that executes one or more safety rules, such as safety rules 916. For instance, rule engine 918 may determine which safety rules to execute based on context data, information included in the safety rule set, other information received from PPEMS 906 or other computing devices, user input from the worker, or any other source of data that indicates which safety rules to execute. In some examples, safety rules 916 may be installed prior to a worker entering a work environment, while in other examples, safety rules 916 be dynamically retrieved by mobile computing device 902 based on context data generated at first particular point in time.

Rule engine 918 may execute safety rules periodically, continuously, or asynchronously. For instance, rule engine 918 may execute safety rules periodically by evaluating the conditions of such rules each time a particular time interval passes or expires (e.g., every second, every minute, etc.). In some examples, rule engine 918 may execute safety rules continuously by checking such conditions using one or more scheduling techniques that continuously evaluate the conditions of such rules. In some examples, rule engine 918 may execute safety rules asynchronously, such as in response to detecting an event. An event may be any detectable occurrence, such as moving to a new location, detecting a worker, coming within a threshold distance of another object, or any other detectable occurrence.

Rule engine 918, upon determining that a condition of a safety rule has or has not been satisfied may perform one or more actions associated with the safety rule by executing one or more operations that define the actions. For instance, rule engine 918 may execute a condition that determines if a worker is approaching or has entered a work environment, (a) whether a PAPR is being worn by the worker and (b) whether the filter in the PAPR of a particular type of filter, e.g., a filter that removes contaminants of a particular type. This safety rule may specify actions if the condition is not satisfied which cause rule engine 918 to generate an alert at mobile computing device 902 using UI device 910 and send a message using communication unit 905 to PPEMS 906, which may cause PPEMS 906 to send a notification to a remote user (e.g., the safety manager).

Alert data 920 may be used for generating alerts for output by UI device 910. For example, mobile computing device

902 may receive alert data from PPEMS 706, end-user computing devices 716, remote users using computing devices 718, safety stations 715, or other computing devices as illustrated in FIG. 7. In some examples, alert data 920 may be based on operation of system 900. For example, mobile computing device 902 may receive alert data 920 that indicates a status of system 900, that system 900 is appropriate for the environment in which system 900 is located, that the environment in which system 900 is located is unsafe, or the like.

In some examples, additionally or alternatively, mobile computing device 902 may receive alert data 920 associated with a likelihood of a safety event. For example, as noted above, PPEMS 906 may, in some examples, apply historical data and models to usage data from system 900 in order to compute assertions, such as anomalies or predicted occurrences of imminent safety events based on environmental conditions or behavior patterns of a worker using system 900. That is, PPEMS 906 may apply analytics to identify relationships or correlations between sensed data from system 900, environmental conditions of environment in which system 900 is located, a geographic region in which system 900 is located, and/or other factors. PPEMS 906 may determine, based on the data acquired across populations of workers 910, which particular activities, possibly within certain environment or geographic region, lead to, or are predicted to lead to, unusually high occurrences of safety events. Mobile computing device 902 may receive alert data 920 from PPEMS 906 that indicates a relatively high likelihood of a safety event.

Alert engine 922 may be a combination of hardware and software that interprets alert data 920 and generate an output at UI device 910 (e.g., an audible, visual, or tactile output) to notify worker 910 of the alert condition (e.g., that the likelihood of a safety event is relatively high, that the environment is dangerous, that system 900 is malfunctioning, that one or more components of system 900 need to be repaired or replaced, or the like). In some instances, alert engine 922 may also interpret alert data 920 and issue one or more commands to system 900 to modify operation or enforce rules of system 900 in order to bring operation of system 900 into compliance with desired/less risky behavior. For example, alert engine 922 may issue commands that control the operation of head top 926 or a clean air supply source.

In some embodiments in accordance with this disclosure, system 900 includes hearing protection 928 (such as earmuffs 10 as shown in FIG. 1) incorporating one or more physiological sensors (such as sensors 650 as shown in FIGS. 5A, 5B, and 6), as well as a computing device 902 including processing circuitry 904 (such as processing circuitry 580 as shown in FIG. 5B) configured to process and analyze data from the physiological sensors. For example, each of muff cups 936 may include a cushion (such as cushion 70 as shown in FIGS. 5A, 5B, and 6) embedded with one or more physiological sensors (such as sensor 650 as shown in FIGS. 5A, 5B, and 6). In some examples, a physiological sensor may include a PPG sensor and/or other optical sensor configured to measure the blood oximetry and/or other biomarkers of a wearer, such as worker 910. In some examples, a physiological sensor may include an EEG and/or EDA sensor and electrodes configured to monitor the brain activity and/or electrodermal activity of a wearer, such as worker 910.

In the example depicted in FIG. 9, system 900 includes a computing device 900 having processing circuitry 904 configured to process and analyze data from one or more physiological sensors embedded within the muffs 936 of hearing protector 928. Although FIG. 900 depicts computing device 902 as a mobile phone, such as a smartphone, computing device 902, including its various processing and memory components, may instead be incorporated within the one or more physiological sensors disposed directly inside hearing protection 928. In this example, sensors 912 of computing device 902 would include the physiological sensors, such as a PPG sensor, an EEG sensor, EDA sensor, and/or other optical or electrophysiological sensor.

In some examples, computing device 902 includes processing circuitry 904 configured to monitor data from sensors 912. For example, processor 904 and/or rule engine 918 may continuously or periodically compare measurements from sensors 912 to a set of threshold sensor measurements stored within safety rules 916. In the event that processor 904 determines a match—i.e. that a recent sensor measurement is at or above a predetermined threshold level, indicating a significant probability of a physiological condition of worker 910, alert engine 922 may retrieve alert data 920 to generate an alert to notify worker 910 and/or a safety supervisor. Computing device 902 may further store records of measurements and generated alerts within storage device 908 for long-term data processing, including pattern recognition.

The following clauses provide some examples of the disclosure.

Clause 1: A ring-shaped cushion for a hearing protector or audio headset comprising a contact pad for sealing on a wearer's head and an attachment for sealing with an earmuff, the cushion further having a sound insulation tube that inwardly defines an inner space, wherein the inner space corresponds to a space that is encircled by the sound insulation tube, the sound insulation tube being ring-shaped and extending between the contact pad and the attachment wherein the sound insulation tube forms the only ring-shaped airtight seal connecting the contact pad and the attachment, and wherein the cushion comprises a ventilation passage extending entirely through the cushion between an inlet opening in the contact pad and an area outside of the inner space.

Clause 2: The cushion of clause 1, further comprising a plurality of inlet openings, wherein the ventilation passage extends between the plurality of inlet openings in the contact pad and an area outside of the inner space.

Clause 3: The cushion of clause 2, wherein the inlet opening or the inlet openings provide an open area, wherein the contact pad outside the inlet opening(s) provides a surface area, and wherein the ratio of the open area relative to the surface area is within a range of 30% to 45%.

Clause 4: The cushion of any of clauses 1-3, wherein the contact pad protrudes radially outwardly from a proximal side of the sound insulation tube, and the sound insulation tube and the contact pad are preferably monolithically formed in one piece.

Clause 5: The cushion of any of clauses 1-4, wherein the cushion adjacent an outer circumference of the contact pad further comprises a circumferential collar protruding from the contact pad in a direction toward the attachment, wherein the collar and the contact pad are preferably monolithically formed in one piece.

Clause 6: The cushion of clause 5, wherein a gap is provided between a free end of the collar and the attachment, and a compression of the cushion causes the gap to close such that the contact pad is supported on the attachment via the collar.

Clause 7: The cushion of any of clauses 5-6, wherein the collar in a direction away from the contact pad tapers.

Clause 8: The cushion of any of clauses 5-7, wherein the collar comprises one or a plurality of outlet openings of the ventilation passage.

Clause 9: The cushion of any of clauses 1-8, wherein the attachment comprises a seal for sealing with an earmuff.

Clause 10: The cushion of any of clauses 1-9, wherein the cushion is homogenously molded.

Clause 11: The cushion of clause 9, further comprising a mounting ring and an attachment flange protruding radially outwardly from a distal side of the sound insulation tube, wherein the mounting ring comprises the seal and wherein the attachment flange is sealingly attached on the mounting ring, and wherein the sound insulation tube and the attachment flange are preferably monolithically formed in one piece.

Clause 12: The cushion of any of clauses 1-11, wherein the contact pad is made of a material exhibiting a Shore hardness A within a range of 20 to 40.

Clause 13: The cushion of clause 12, wherein the contact pad is made of silicone.

Clause 14: The cushion of any of clauses 1-13, wherein the cushion further comprises, adjacent the attachment of the cushion, a nonporous and cup-shaped sound attenuator for insertion into an earmuff, the sound attenuator having an outer attenuator shell and a plurality of sound-attenuating structures which protrude from the attenuator shell.

Clause 15: The cushion of clause 14, wherein the cushion is monolithically formed in one piece with the sound attenuator.

Clause 16: The cushion of any of clauses 1-15, wherein the cushion further comprises a circumferential resilient dividing wall protruding from the contact pad in a direction toward the attachment, providing a gap between a free end of the dividing wall and the attachment, and wherein a compression of the cushion causes the gap to close such that a closed volume is formed between the dividing wall and the sound insulation tube.

Clause 17: The cushion of clause 1, wherein the cushion further comprises at least one physiological sensor disposed within the ventilation passage that extends entirely through the cushion, wherein the at least one physiological sensor is configured to generate signal data associated with one or more physiological parameters of the wearer.

Clause 18: The cushion of clause 17, wherein the at least one physiological sensor is powered with a battery that is disposed inside the cushion.

Clause 19: The cushion of clause 17, wherein the at least one physiological sensor is powered by a power source of the earmuff.

Clause 20: The cushion of any of clauses 17-19, wherein the at least one physiological sensor comprises at least one electroencephalogram (EEG) electrode that generates the signal data associated with the one or more physiological parameters of the wearer, wherein the one or more physiological parameters comprise brain wave signals.

Clause 21: The cushion of clause 20, wherein the brain wave signals indicate a state of fatigue of the wearer by indicating at least one of fatigue, drowsiness, or excessive blinking of eyes.

Clause 22: The cushion of any of clauses 20-21, wherein the at least one EEG electrode comprises at least four EEG electrodes.

Clause 23: The cushion of any of clauses 17-22, wherein the at least one physiological sensor comprises at least one electrodermal activity (EDA) electrode that generates the signal data associated with the one or more physiological parameters of the wearer, and the one or more physiological parameters comprise electrodermal response signals that support an indication of a state of fatigue of the wearer.

Clause 24: The cushion of clause 23, wherein the at least one EDA electrode comprises at least two EDA electrodes.

Clause 25: The cushion of any of clauses 17-24, wherein the at least one physiological sensor comprises an optical sensor that is configured to generate the signal data associated with the one or more physiological parameters of the wearer, and the one or more physiological parameters comprise a biomarker of the wearer.

Clause 26: The cushion of any of clauses 17-25, wherein the at least one physiological sensor comprises a photoplethysmograph (PPG) sensor that is configured to generate the signal data associated with the one or more physiological parameters of the wearer, and the one or more physiological parameters comprise at least one of a pulse, a blood oxygen saturation, or a core body temperature of the wearer.

Clause 27: The cushion of any of clauses 17-26, wherein the at least one physiological sensor is positioned within the ventilation passage at least partially below the inlet opening.

Clause 28: The cushion of any of clauses 17-27, wherein the cushion further comprises a communication module that is configured to output the at least one signal to one or more of the hearing protector, the audio headset, or an external computing system.

Clause 29: A hearing protector comprising two earmuffs, wherein a cushion according to any of the preceding claims is mounted to each of the earmuffs.

Clause 30: The hearing protector of clause 29, further comprising at least one physiological sensor disposed within each of the two earmuffs, wherein the physiological sensors are of a same type or of different types.

Clause 31: The hearing protector of any of clauses 29-30, wherein the hearing protector further comprises a headband, wherein the cushions, the headband and the earmuffs are each made from a respective heat-resistant material, such as a plastic material or a metal, that can withstand industrial washing at 85° C.

Clause 32: A system comprising a hearing protector comprising two earmuffs for positioning on a head of a wearer, a cushion according to clause 17, and a computing device with processing circuitry configured to receive, from the at least one physiological sensor, the signal data associated with the one or more physiological parameters of the wearer, and output, based on the signal data, an alert associated with a physiological condition of the wearer.

Clause 33: The system of clause 32, wherein the computing device is further configured to determine, based on the signal data, a probability of the physiological condition of the wearer, and, responsive to determining that the probability exceeds a threshold, output the alert associated with the physiological condition of the user.

Clause 34: The system of clause 33, wherein the computing device is further configured to send the signal data to an external computing system via a cloud network, receive, from the external computing system, an indication of the physiological condition of the wearer, and responsive to receiving the indication, output the alert.

Clause 35: The system of any of clauses 32-34, wherein the computing device is configured to output the alert associated with the physiological condition of the wearer via a communication module of at least one of the two earmuffs.

Clause 36: The system of any of clauses 32-35, wherein the alert comprises a visual or haptic alert.

Clause 37: The system of any of clauses 32-36, wherein the computing device is further configured to send, to an external device used by the wearer or another user, an indication of the alert associated with the physiological condition of the wearer.

Clause 38: The system of any of clauses 32-37, wherein the at least one physiological sensor comprises at least one electroencephalogram (EEG) electrode that generates the signal data associated with the one or more physiological parameters of the wearer, wherein the one or more physiological parameters comprise brain wave signals.

Clause 39: The system of clause 38, wherein the brain wave signals indicate a state of fatigue of the wearer by indicating at least one of fatigue, drowsiness, or excessive blinking of eyes, and wherein the physiological condition associated with the alert comprises a threshold level of fatigue of the wearer.

Clause 40: The system of any of clauses 32-39, wherein the at least one physiological sensor comprises at least one electrodermal activity (EDA) electrode that generates the signal data associated with the one or more physiological parameters of the wearer, the one or more physiological parameters comprise electrodermal signals that support the indication of a state of fatigue of the wearer, and the physiological condition associated with the alert comprises a threshold level of fatigue of the wearer.

Clause 41: The system of any of clauses 32-40, wherein the at least one physiological sensor comprises an optical sensor that is configured to generate the signal data associated with the one or more physiological parameters of the wearer, the one or more physiological parameters comprise a biomarker of the wearer, and the physiological condition associated with the alert comprises a threshold level of distress of the wearer.

Clause 42: The system of any of clauses 32-41, wherein the at least one physiological sensor comprises a photoplethysmograph (PPG) sensor that is configured to generate the signal data associated with the one or more physiological parameters of the wearer, the one or more physiological parameters comprise at least one of a pulse, a blood oxygen saturation, or a core body temperature of the wearer, and the physiological condition associated with the alert comprises a threshold level of distress of the wearer.

Clause 43: The system of any of clauses 32-42, wherein the at least one physiological sensor is positioned within the ventilation passage at least partially below the inlet opening.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

The invention claimed is:

1. A ring-shaped cushion for a hearing protector or audio headset, comprising a contact pad for sealing on a wearer's head and an attachment for sealing with an earmuff, the cushion further having a sound insulation tube that inwardly defines an inner space, wherein the inner space corresponds to a space that is encircled by the sound insulation tube, the sound insulation tube being ring-shaped and extending between the contact pad and the attachment wherein the sound insulation tube forms the only ring-shaped airtight seal connecting the contact pad and the attachment, and wherein the cushion comprises a ventilation passage extending entirely through the cushion between an inlet opening in the contact pad and an area outside of the inner space, the cushion further comprising a circumferential resilient dividing wall protruding from the contact pad in a direction toward the attachment, providing a gap between a free end of the dividing wall and the attachment and wherein a compression of the cushion causes the gap to close such that a closed volume is formed between the dividing wall and the sound insulation tube.

2. The cushion of claim 1, comprising a plurality of inlet openings, wherein the ventilation passage extends between the plurality of inlet openings in the contact pad and an area outside of the inner space.

3. The cushion of claim 2, wherein at least one of the plurality of inlet openings provides an open area and wherein the contact pad outside the at least one of the plurality of inlet openings provides a surface area, and wherein the ratio of the open area relative to the surface area is within a range of 30% to 45%.

4. The cushion of claim 1, wherein the contact pad protrudes radially outwardly from a proximal side of the sound insulation tube, and wherein the sound insulation tube and the contact pad are monolithically formed in one piece.

5. The cushion of claim 1, wherein the cushion adjacent an outer circumference of the contact pad further comprises a circumferential collar protruding from the contact pad in a direction toward the attachment, wherein the collar and the contact pad are monolithically formed in one piece.

6. The cushion of claim 1, wherein the attachment comprises a seal for sealing the earmuff.

7. The cushion of claim 1, wherein the cushion is homogenously molded.

8. The cushion of claim 1, wherein the contact pad is made of a material exhibiting a Shore hardness A within a range of 20 to 40.

9. The cushion of claim 1, further comprising adjacent the attachment of the cushion a nonporous and cup-shaped sound attenuator for insertion into the earmuff, the sound attenuator having an outer attenuator shell and a plurality of sound-attenuating structures which protrude from the attenuator shell.

10. A ring-shaped cushion for a hearing protector or audio headset, comprising a contact pad for sealing on a wearer's head and an attachment for sealing with an earmuff, the cushion further having a sound insulation tube that inwardly defines an inner space, wherein the inner space corresponds to a space that is encircled by the sound insulation tube, the sound insulation tube being ring-shaped and extending between the contact pad and the attachment wherein the sound insulation tube forms the only ring-shaped airtight seal connecting the contact pad and the attachment, and wherein the cushion comprises a ventilation passage extending entirely through the cushion between an inlet opening in the contact pad and an area outside of the inner space;
wherein the cushion adjacent an outer circumference of the contact pad further comprises a circumferential collar protruding from the contact pad in a direction toward the attachment, wherein the collar and the contact pad are monolithically formed in one piece;
wherein a gap is provided between a free end of the collar and the attachment, and wherein a compression of the cushion causes the gap to close such that the contact pad is supported on the attachment via the collar.

11. A ring-shaped cushion for a hearing protector or audio headset, comprising a contact pad for sealing on a wearer's head and an attachment for sealing with an earmuff, the cushion further having a sound insulation tube that inwardly defines an inner space, wherein the inner space corresponds to a space that is encircled by the sound insulation tube, the sound insulation tube being ring-shaped and extending between the contact pad and the attachment wherein the sound insulation tube forms the only ring-shaped airtight seal connecting the contact pad and the attachment and wherein the cushion comprises a ventilation passage extending entirely through the cushion between an inlet opening in the contact pad and an area outside of the inner space;
further comprising at least on physiological sensor disposed within the ventilation passage that extends entirely through the cushion, wherein the at least one physiological sensor is configured to generate signal data associated with one or more physiological parameters of the wearer,
wherein the at least one physiological sensor is selected from the group consisting of:
at least one electroencephalogram (EEG) electrode that generates the signal data associated with the one or more physiological parameters of the wearer, wherein the one or more physiological parameters comprise brain wave signals;
at least one electrodermal activity (EDA) electrode that generates the signal data associated with the one or more physiological parameters of the wearer, wherein the one or more physiological parameters comprise electrodermal response signals that support an indication of a state of fatigue of the wearer;
an optical sensor that is configured to generate the signal data associated with the one or more physiological parameters of the wearer, wherein the one or more physiological parameters comprise a biomarker of the wearer; and
a photoplethysmograph (PPG) sensor that is configured to generate the signal data associated with the one or more physiological parameters of the wearer, wherein the one or more physiological parameters comprise at least one of a pulse, a blood oxygen saturation, or a core body temperature of the wearer.

12. The cushion of claim 11, wherein the at least one physiological sensor is powered with a battery that is disposed inside the cushion.

13. The cushion of claim 11, wherein the at least one physiological sensor is powered by a power source of the earmuff.

14. The cushion of claim 11, further comprising a communication module that is configured to output the signal data to one or more of the hearing protector, the audio headset, or an external computing system.

15. A hearing protector, comprising two earmuffs, wherein a cushion according claim 11 is mounted to each of the earmuffs.

16. A system comprising:
a hearing protector comprising two earmuffs for positioning on a head of a wearer;
a cushion according to claim 11; and
a computing device with processing circuitry configured to:
receive, from the at least one physiological sensor, the signal data associated with the one or more physiological parameters of the wearer; and
output, based on the signal data, an alert associated with a physiological condition of the wearer.

17. The system of claim 16, wherein the computing device is further configured to:
determine, based on the signal data, a probability of the physiological condition of the wearer; and
responsive to determining that the probability exceeds a threshold, output the alert associated with the physiological condition of the user.

18. The system of claim 17, wherein the computing device is further configured to:
send the signal data to an external computing system via a cloud network;
receive, from the external computing system, an indication of the physiological condition of the wearer; and
responsive to receiving the indication, output the alert.

* * * * *

UNITED STATES PATENT AND TRADEMARK OFFICE
CERTIFICATE OF CORRECTION

PATENT NO. : 11,582,548 B2
APPLICATION NO. : 15/733080
DATED : February 14, 2023
INVENTOR(S) : Cuong Bui et al.

Page 1 of 1

It is certified that error appears in the above-identified patent and that said Letters Patent is hereby corrected as shown below:

In the Claims

Column 49
Line 60, In Claim 11, delete "on" and insert -- one --, therefor.

Signed and Sealed this
Eighth Day of August, 2023

Katherine Kelly Vidal
*Director of the United States Patent and Trademark Office*